United States Patent
Dickinson et al.

(10) Patent No.: US 7,714,120 B2
(45) Date of Patent: May 11, 2010

(54) HUMANIZED ANTI-IL-1 BETA ANTIBODIES

(75) Inventors: Craig Duane Dickinson, San Diego, CA (US); Alain Philippe Vasserot, Carlsbad, CA (US); Jeffry Dean Watkins, Encinitas, CA (US); Jirong Lu, Indianapolis, IN (US)

(73) Assignee: Applied Molecule Evolution, Inc., San Diego, CA (US)

( * ) Notice: Subject to any disclaimer, the term of this patent is extended or adjusted under 35 U.S.C. 154(b) by 0 days.

(21) Appl. No.: 12/428,558

(22) Filed: Apr. 23, 2009

(65) Prior Publication Data
US 2009/0209004 A1 Aug. 20, 2009

Related U.S. Application Data

(62) Division of application No. 10/542,508, filed as application No. PCT/US2004/000019 on Jan. 24, 2004, now Pat. No. 7,541,033.

(51) Int. Cl.
*C07H 21/04* (2006.01)
*C12P 21/06* (2006.01)
*C12N 15/74* (2006.01)

(52) U.S. Cl. .................. 536/23.53; 536/23.1; 536/23.5; 435/320.1; 435/328; 435/69.1; 435/69.6

(58) Field of Classification Search ........................ None
See application file for complete search history.

(56) References Cited

U.S. PATENT DOCUMENTS

| | | |
|---|---|---|
| 4,935,343 A | 6/1990 | Allison et al. |
| 5,225,539 A | 7/1993 | Winter |
| 5,484,887 A | 1/1996 | Kronheim et al. |
| 5,681,933 A | 10/1997 | Auron et al. |
| 6,054,297 A | 4/2000 | Carter et al. |
| 6,248,516 B1 | 6/2001 | Winter et al. |

FOREIGN PATENT DOCUMENTS

| | | |
|---|---|---|
| WO | WO 95/01997 | 1/1995 |
| WO | WO 01/64751 | 9/2001 |
| WO | WO 03/010282 | 2/2003 |
| WO | WO 03/073982 | 9/2003 |

OTHER PUBLICATIONS

Jackson, Jeffrey R., et a., In Vitro Antibody Maturation—Improvement of a High Affinity, Neutralizing Antibody Against IL-1β. *Journal of Immunology*, vol. 154, pp. 3310-3319 (1995).

Boraschi et al., "A Monoclonal Antibody to the IL-1β peptide 163-171 Blocks Adjuvanticity but not Pyrogenicity of IL-1β in vivo," *Journal of Immunology*, vol. 143, pp. 131-134 (1989).

Owens et al., *Journal of Immunological Methods*, "The genetic engineering of monoclonal antibodies," vol. 168, pp. 149-165 (1994).

*Primary Examiner*—Phillip Gambel
*Assistant Examiner*—Sharon Wen
(74) *Attorney, Agent, or Firm*—Andrea M. Castetter

(57) ABSTRACT

The present invention encompasses isolated antibodies, or antigen-binding portions thereof, that specifically bind mature human IL-1 Beta. These antibodies, or antigen-binding portions thereof, generally exhibit high binding affinities (low $k_{o}ff$ values), reduced deamidation compared to the native antibody, and can be used to treat various diseases such as rheumatoid arthritis, osteoarthritis, or neuroinflammation.

8 Claims, No Drawings

```
                              SEQUENCE LISTING

<160> NUMBER OF SEQ ID NOS: 68

<210> SEQ ID NO 1
<211> LENGTH: 11
<212> TYPE: PRT
<213> ORGANISM: Murine

<400> SEQUENCE: 1

Lys Ala Ser Gln Asp Ile Asp Arg Tyr Leu Ser
1               5                   10

<210> SEQ ID NO 2
<211> LENGTH: 7
<212> TYPE: PRT
<213> ORGANISM: Murine

<400> SEQUENCE: 2

Arg Val Lys Arg Leu Val Asp
1               5

<210> SEQ ID NO 3
<211> LENGTH: 9
<212> TYPE: PRT
<213> ORGANISM: Murine

<400> SEQUENCE: 3

Leu Gln Tyr Asp Glu Phe Pro Tyr Thr
1               5

<210> SEQ ID NO 4
<211> LENGTH: 10
<212> TYPE: PRT
<213> ORGANISM: Murine

<400> SEQUENCE: 4

Gly Tyr Thr Phe Ser Arg Tyr Trp Ile Glu
1               5                   10

<210> SEQ ID NO 5
<211> LENGTH: 17
<212> TYPE: PRT
<213> ORGANISM: Murine

<400> SEQUENCE: 5

Glu Ile Leu Pro Gly Asn Gly Asn Ile Asn Tyr Asn Glu Lys Phe Lys
1               5                   10                  15

Gly

<210> SEQ ID NO 6
<211> LENGTH: 11
<212> TYPE: PRT
<213> ORGANISM: Murine

<400> SEQUENCE: 6

Ile Tyr Tyr Asp Tyr Asp Gln Gly Phe Thr Tyr
1               5                   10
```

<210> SEQ ID NO 7
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 7

Val Gln Tyr Asp Glu Phe Asn Tyr Thr
1               5

<210> SEQ ID NO 8
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 8

Glu Ile Leu Pro Gly Thr Gly Thr Ile Asn Tyr Asn Glu Lys Phe Lys
1               5                   10                  15

Gly

<210> SEQ ID NO 9
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 9

Val Tyr Tyr Asp Tyr Asp Tyr Gly Phe Asp Tyr
1               5                   10

<210> SEQ ID NO 10
<211> LENGTH: 10
<212> TYPE: PRT
<213> ORGANISM: ARTIFICIAL SEQUENCE
<220> FEATURE:
<223> OTHER INFORMATION: Synthetic Construct

<400> SEQUENCE: 10

Gly Tyr Thr Phe Asp Arg Tyr Trp Ile Glu
1               5                   10

<210> SEQ ID NO 11
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 11

Val Tyr Tyr Asp Tyr Asp Tyr Gly Phe Asp Leu
1               5                   10

<210> SEQ ID NO 12
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 12

Lys Ala Ser Gln Asp Ile Asp Arg Tyr Leu Thr
1               5                   10

<210> SEQ ID NO 13
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 13

Ile Gln Tyr Asp Glu Phe Asn Tyr Thr
1               5

<210> SEQ ID NO 14
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 14

Val Tyr Tyr Asp Tyr Asp Tyr Gly Phe Asp Asn
1               5                   10

<210> SEQ ID NO 15
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 15

Ile Gln Tyr Asp Glu Phe Pro Tyr Thr
1               5

<210> SEQ ID NO 16
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 16

Glu Ile Leu Pro Gly Ser Gly Thr Ile Asn Tyr Asn Glu Lys Phe Lys
1               5                   10                  15

Gly

<210> SEQ ID NO 17
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 17

Val Gln Tyr Asp Glu Phe Pro Tyr Thr
1               5

<210> SEQ ID NO 18
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 18

Glu Ile Leu Pro Gly Thr Gly Asp Ile Asn Tyr Asn Glu Lys Phe Lys

```
                1               5                  10                 15

Gly

<210> SEQ ID NO 19
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 19

Val Tyr Tyr Asp Tyr Asp Tyr Gly Phe Thr Leu
1               5                  10

<210> SEQ ID NO 20
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 20

Ile Gln Tyr Asp Glu Phe Pro Tyr Leu
1               5

<210> SEQ ID NO 21
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 21

Glu Ile Leu Pro Gly Ser Gly Asp Ile Asn Tyr Asn Glu Lys Phe Lys
1               5                  10                 15

Gly

<210> SEQ ID NO 22
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 22

Lys Phe Ser Gln Asp Ile Asp Arg Tyr Leu Thr
1               5                  10

<210> SEQ ID NO 23
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 23

Glu Ile Leu Pro Gly Ser Gly Asn Ile Asn Tyr Asn Glu Lys Phe Lys
1               5                  10                 15

Gly

<210> SEQ ID NO 24
<211> LENGTH: 11
<212> TYPE: PRT
<213> ORGANISM: ARTIFICIAL SEQUENCE
<220> FEATURE:
```

<223> OTHER INFORMATION: Synthetic Construct

<400> SEQUENCE: 24

Val Tyr Tyr Asp Tyr Asp Gln Gly Phe Asp Asn
1               5                   10

<210> SEQ ID NO 25
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 25

Val Gln Tyr Asp Glu Phe Pro Tyr Leu
1               5

<210> SEQ ID NO 26
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 26

Val Tyr Tyr Asp Tyr Asp Tyr Gly Phe Thr Tyr
1               5                   10

<210> SEQ ID NO 27
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 27

Val Tyr Tyr Asp Tyr Asp Tyr Gly Phe Thr Asn
1               5                   10

<210> SEQ ID NO 28
<211> LENGTH: 17
<212> TYPE: PRT
<213> ORGANISM: ARTIFICIAL SEQUENCE
<220> FEATURE:
<223> OTHER INFORMATION: Synthetic Construct

<400> SEQUENCE: 28

Glu Ile Leu Pro Gly Thr Gly Asn Ile Asn Tyr Asn Glu Lys Phe Lys
1               5                   10                  15

Gly

<210> SEQ ID NO 29
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 29

Lys Ala Ser Gln Asp Ile Asp Arg Phe Leu Ser
1               5                   10

<210> SEQ ID NO 30
<211> LENGTH: 11
<212> TYPE: PRT
<213> ORGANISM: ARTIFICIAL SEQUENCE

```
<220> FEATURE:
<223> OTHER INFORMATION: Synthetic Construct

<400> SEQUENCE: 30

Met Tyr Tyr Asp Tyr Asp Gln Gly Phe Ser Leu
1               5                   10

<210> SEQ ID NO 31
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 31

Lys Ala Ser Gln Asp Ile Asp Arg Phe Leu Thr
1               5                   10

<210> SEQ ID NO 32
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 32

Met Tyr Tyr Asp Tyr Asp Gln Gly Phe Thr Asn
1               5                   10

<210> SEQ ID NO 33
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 33

Lys Ala Ser Gln Asp Ile Asp Arg Phe Leu Ser
1               5                   10

<210> SEQ ID NO 34
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 34

Val Gln Tyr Asp Glu Phe Ala Tyr Thr
1               5

<210> SEQ ID NO 35
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 35

Met Tyr Tyr Asp Tyr Asp Gln Gly Phe Asp Tyr
1               5                   10

<210> SEQ ID NO 36
<211> LENGTH: 11
<212> TYPE: PRT
<213> ORGANISM: ARTIFICIAL SEQUENCE
<220> FEATURE:
```

```
<223> OTHER INFORMATION: Synthetic Construct

<400> SEQUENCE: 36

Met Tyr Tyr Asp Tyr Asp Gln Gly Phe Asp Asn
1               5                   10

<210> SEQ ID NO 37
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 37

Lys Phe Ser Gln Asp Ile Asp Arg Phe Leu Thr
1               5                   10

<210> SEQ ID NO 38
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 38

Met Tyr Tyr Asp Tyr Asp Gln Gly Phe Asp Leu
1               5                   10

<210> SEQ ID NO 39
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 39

Lys Phe Ser Gln Asp Ile Asp Arg Phe Leu Ser
1               5                   10

<210> SEQ ID NO 40
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 40

Met Tyr Tyr Asp Tyr Asp Gln Gly Phe Thr Leu
1               5                   10

<210> SEQ ID NO 41
<211> LENGTH: 9
<212> TYPE: PRT
<213> ORGANISM: ARTIFICIAL SEQUENCE
<220> FEATURE:
<223> OTHER INFORMATION: Synthetic Construct

<400> SEQUENCE: 41

Val Gln Tyr Asp Glu Phe Pro Tyr Gly
1               5

<210> SEQ ID NO 42
<211> LENGTH: 11
<212> TYPE: PRT
<213> ORGANISM: ARTIFICIAL SEQUENCE
<220> FEATURE:
<223> OTHER INFORMATION: Synthetic Construct
```

<400> SEQUENCE: 42

Met Tyr Tyr Asp Tyr Asp Gln Gly Phe Thr Tyr
1               5                   10

<210> SEQ ID NO 43
<211> LENGTH: 387
<212> TYPE: DNA
<213> ORGANISM: Murine

<400> SEQUENCE: 43
atggacatga ggacccctgc tcagtttctt ggaatctttt tcttctggtt tccaggtatc      60
agatgtgaca tcaagatgac ccagtctcca tcttccatgt atgcatctct aggagagaga     120
gtcactatca cttgcaaggc gagtcaggac attgataggt atttaagttg gttccagcag     180
aaaccaggga atctcctaa gaccctgatc tatcgtgtaa agagattggt agatggggtc      240
ccatcaaggt tcagtggcag cgcatctggg caagattatt ctctcaccat cagcagcctg     300
cagtatgaag atatgggaat ttattattgt ctacagtatg atgagtttcc gtacacgttc     360 ggaggggga ccaagctgga aataaaa                                           387

<210> SEQ ID NO 44
<211> LENGTH: 417
<212> TYPE: DNA
<213> ORGANISM: Murine

<400> SEQUENCE: 44
atggaatgga cctgggtctt tctcttcctc ctgtcagtaa ctgcaggtgt ccactcccag      60
gttcagctgc agcagtctgg agctgagctg atgaagcctg gggcctcagt gaagatatcc     120
tgcaaggcta ctggctacac attcagtagg tattggatag agtggataaa gcagaggcct     180
ggacatggcc ttgagtggat tggagagatt ttacctggaa atggaaatat taactacaat     240
gagaagttca agggcaaggc cacaatctct gcagattctt cctccgaaac agcctacatg     300
caactcagca gcctgtcctc tgaggactct gccgtctatt attgttcaac aatctactat     360
gattacgacc aggggtttac ttactggggc caagggactc tggtcactgt ttctgca        417

<210> SEQ ID NO 45
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asp Arg Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Asp Ile Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Tyr Asp Tyr Asp Gln Gly Phe Asp Tyr Trp Gly Gln

-continued

```
               100                 105                 110
Gly Thr Leu Val Thr Val Ser Ser Ala Ser Thr Lys Gly Pro Ser Val
           115                 120                 125

Phe Pro Leu Ala Pro Ser Ser Lys Ser Thr Ser Gly Gly Thr Ala Ala
       130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
               165                 170                 175

Leu Gln Ser Ser Gly Leu Tyr Ser Leu Ser Ser Val Val Thr Val Pro
           180                 185                 190

Ser Ser Ser Leu Gly Thr Gln Thr Tyr Ile Cys Asn Val Asn His Lys
       195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
               245                 250                 255

Ser Arg Thr Pro Glu Val Thr Cys Val Val Val Asp Val Ser His Glu
           260                 265                 270

Asp Pro Glu Val Lys Phe Asn Trp Tyr Val Asp Gly Val Glu Val His
       275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
               325                 330                 335

Lys Thr Ile Ser Lys Ala Lys Gly Gln Pro Arg Glu Pro Gln Val Tyr
           340                 345                 350

Thr Leu Pro Pro Ser Arg Asp Glu Leu Thr Lys Asn Gln Val Ser Leu
       355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
               405                 410                 415

Lys Ser Arg Trp Gln Gln Gly Asn Val Phe Ser Cys Ser Val Met His
           420                 425                 430

Glu Ala Leu His Asn His Tyr Thr Gln Lys Ser Leu Ser Leu Ser Pro
       435                 440                 445

Gly Lys
    450
```

<210> SEQ ID NO 46
<211> LENGTH: 214
<212> TYPE: PRT
<213> ORGANISM: ARTIFICIAL SEQUENCE
<220> FEATURE:
<223> OTHER INFORMATION: Synthetic Construct

<400> SEQUENCE: 46

Asp Ile Gln Met Thr Gln Ser Pro Ser Ser Leu Ser Ala Ser Val Gly

```
1               5                   10                  15
Asp Arg Val Thr Ile Thr Cys Lys Phe Ser Gln Asp Ile Asp Arg Phe
                20                  25                  30

Leu Thr Trp Phe Gln Gln Lys Pro Gly Lys Ala Pro Lys Ser Leu Ile
                35                  40                  45

Tyr Arg Val Lys Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ile Gln Tyr Asp Glu Phe Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 47
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asp Arg Tyr
                20                  25                  30

Trp Ile Glu Trp Val Arg Gln Ala Pro Gly Gln Gly Leu Glu Trp Met
                35                  40                  45

Gly Glu Ile Leu Pro Gly Ser Gly Asp Ile Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Tyr Asp Tyr Asp Gln Gly Phe Asp Leu Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 48
<211> LENGTH: 214
<212> TYPE: PRT
<213> ORGANISM: ARTIFICIAL SEQUENCE
<220> FEATURE:
<223> OTHER INFORMATION: Synthetic Construct

<400> SEQUENCE: 48

Asp Ile Gln Met Thr Gln Ser Pro Ser Ser Leu Ser Ala Ser Val Gly
1               5                   10                  15
Asp Arg Val Thr Ile Thr Cys Lys Phe Ser Gln Asp Ile Asp Arg Phe
            20                  25                  30
Leu Ser Trp Phe Gln Gln Lys Pro Gly Lys Ala Pro Lys Ser Leu Ile
        35                  40                  45
Tyr Arg Val Lys Arg Leu Val Asp Gly Val Pro Ser Arg Phe Ser Gly
```

-continued

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Val Gln Tyr Asp Glu Phe Pro Tyr
                 85                  90                  95

Gly Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 49
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 49

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Asp Arg Tyr
                 20                  25                  30

Trp Ile Glu Trp Val Arg Gln Ala Pro Gly Gln Gly Leu Glu Trp Met
                 35                  40                  45

Gly Glu Ile Leu Pro Gly Ser Gly Thr Ile Asn Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Met Tyr Tyr Asp Tyr Asp Gln Gly Phe Asp Asn Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 50
<211> LENGTH: 213
<212> TYPE: PRT
<213> ORGANISM: ARTIFICIAL SEQUENCE
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Phe Ser Gln Asp Ile Asp Arg Phe
            20                  25                  30

Leu Ser Trp Phe Gln Gln Lys Pro Gly Lys Ala Pro Lys Ser Leu Ile
        35                  40                  45

Tyr Arg Val Lys Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Asp Glu Phe Pro Tyr
                85                  90                  95

Thr Phe Gly Gly Gly Thr Lys Val Glu Ile Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 51
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asp Arg Tyr
                20                  25                  30

Trp Ile Glu Trp Val Arg Gln Ala Pro Gly Gln Gly Leu Glu Trp Met
            35                  40                  45

Gly Glu Ile Leu Pro Gly Ser Gly Asp Ile Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Tyr Asp Tyr Asp Gln Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                    245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 213
<212> TYPE: PRT
<213> ORGANISM: ARTIFICIAL SEQUENCE
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Phe Ser Gln Asp Ile Asp Arg Phe
            20                  25                  30

Leu Ser Trp Phe Gln Gln Lys Pro Gly Lys Ala Pro Lys Ser Leu Ile
        35                  40                  45

Tyr Arg Val Lys Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Asp Glu Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 53
<211> LENGTH: 450
<212> TYPE: PRT
<213> ORGANISM: ARTIFICIAL SEQUENCE
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asp Arg Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Asp Ile Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Tyr Asp Tyr Asp Gln Gly Phe Ser Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                        290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 54
<211> LENGTH: 213
<212> TYPE: PRT
<213> ORGANISM: ARTIFICIAL SEQUENCE
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Arg Phe
            20                  25                  30

Leu Ser Trp Phe Gln Gln Lys Pro Lys Ala Pro Lys Ser Leu Ile Tyr
        35                  40                  45

Arg Val Lys Arg Leu Val Asp Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Val Gln Tyr Asp Glu Phe Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
210

<210> SEQ ID NO 55
<211> LENGTH: 407
<212> TYPE: DNA
<213> ORGANISM: HUMAN

<400> SEQUENCE: 55
ggatccactg gtcaggtgca gctggtgcag tctggcgctg aggtgaagaa gcctggctcc      60
tccgtgaagg tctcctgcaa ggcttctggc tacacattcg accgctattg gatcgagtgg     120
gtgcgccagg cccctggcca aggcctggag tggatgggcg agattctgcc tggcagcggc     180
gacattaact acaatgagaa gttcaagggc cgcgtcacga ttaccgcgga caaatccacg     240
agcacagcct acatggagct gagcagcctg cgctctgagg cacggccgt gtattactgt      300 gcgcgcatgt actatgatta cgaccagggc tttgactact ggggccaggg caccctggtc     360
accgtctcct ccgcctccac caagggccca tcggtcttcc cgctagc                   407

<210> SEQ ID NO 56
<211> LENGTH: 407
<212> TYPE: DNA
<213> ORGANISM: HUMAN

<400> SEQUENCE: 56
ggatccactg gtcaggtgca gctggtgcag tctggcgctg aggtgaagaa gcctggctcc      60
tccgtgaagg tctcctgcaa ggcttctggc tacacattcg accgctattg gatcgagtgg     120
gtgcgccagg cccctggcca aggcctggag tggatgggcg agattctgcc tggcagcggc     180
gacattaact acaatgagaa gttcaagggc cgcgtcacga ttaccgcgga caaatccacg     240
agcacagcct acatggagct gagcagcctg cgctctgagg cacggccgt gtattactgt      300 gcgcgcatgt actatgatta cgaccagggc tttgacctgt ggggccaggg caccctggtc     360
accgtctcct ccgcctccac caagggccca tcggtcttcc cgctagc                   407

<210> SEQ ID NO 57
<211> LENGTH: 407
<212> TYPE: DNA
<213> ORGANISM: HUMAN

<400> SEQUENCE: 57
ggatccactg gtcaggtgca gctggtgcag tctggcgctg aggtgaagaa gcctggctcc      60
tccgtgaagg tctcctgcaa ggcttctggc tacacattcg accgctattg gatcgagtgg     120
gtgcgccagg cccctggcca aggcctggag tggatgggcg agattctgcc tggcagcggc     180
accattaact acaatgagaa gttcaagggc cgcgtcacga ttaccgcgga caaatccacg     240
agcacagcct acatggagct gagcagcctg cgctctgagg cacggccgt gtattactgt      300 gcgcgcatgt actatgatta cgaccagggc tttgacaact ggggccaggg caccctggtc     360
accgtctcct ccgcctccac caagggccca tcggtcttcc cgctagc                   407

<210> SEQ ID NO 58
<211> LENGTH: 407
<212> TYPE: DNA
<213> ORGANISM: HUMAN

<400> SEQUENCE: 58

```
ggatccactg gtcaggtgca gctggtgcag tctggcgctg aggtgaagaa gcctggctcc      60
tccgtgaagg tctcctgcaa ggcttctggc tacacattcg accgctattg gatcgagtgg     120
gtgcgccagg cccctggcca aggcctggag tggatgggcg agattctgcc tggcagcggc     180
gacattaact acaatgagaa gttcaagggc cgcgtcacga ttaccgcgga caaatccacg     240
agcacagcct acatggagct gagcagcctg cgctctgagg cacggccgt gtattactgt      300 gcgcgcatgt actatgatta cgaccagggc tttagcctgt ggggccaggg caccctggtc     360
accgtctcct ccgcctccac caagggccca tcggtcttcc cgctagc                  407

<210> SEQ ID NO 59
<211> LENGTH: 407
<212> TYPE: DNA
<213> ORGANISM: HUMAN

<400> SEQUENCE: 59
ggatccactg gtcaggtgca gctggtgcag tctggcgctg aggtgaagaa gcctggctcc      60
tccgtgaagg tctcctgcaa ggcttctggc tacacattcg accgctattg gatcgagtgg     120
gtgcgccagg cccctggcca aggcctggag tggatgggcg agattctgcc tggcagcggc     180
gacattaact acaatgagaa gttcaagggc cgcgtcacga ttaccgcgga caaatccacg     240
agcacagcct acatggagct gagcagcctg cgctctgagg cacggccgt gtattactgt      300 gcgcgcatgt actatgatta cgaccagggc tttgactact ggggccaggg caccctggtc     360
accgtctcct ccgcctccac caagggccca tcggtcttcc cgctagc                  407

<210> SEQ ID NO 60
<211> LENGTH: 321
<212> TYPE: DNA
<213> ORGANISM: HUMAN

<400> SEQUENCE: 60
gacatccaga tgacccagtc tccatcctcc ctgtctgcat ctgtgggcga ccgcgtcacc      60
atcacttgta agttcagtca ggacattgat cgcttcctga cctggtttca gcagaaacca     120
ggcaaagccc ctaagtccct gatctatcgc gtgaagcgcc tggtggatgg cgtcccatcc     180
cgcttcagcg gcagtggctc tggcacagat ttcactctca ccatcagcag cctgcagcct     240
gaagattttg caacttatta ctgcatccag tatgatgagt ttccgtacac cttcggcggc     300
ggcaccaagg tggagatcaa a                                              321

<210> SEQ ID NO 61
<211> LENGTH: 321
<212> TYPE: DNA
<213> ORGANISM: HUMAN

<400> SEQUENCE: 61
gacatccaga tgacccagtc tccatcctcc ctgtctgcat ctgtgggcga ccgcgtcacc      60
atcacttgta agttcagtca ggacattgat cgcttcctga gctggtttca gcagaaacca     120
ggcaaagccc ctaagtccct gatctatcgc gtgaagcgcc tggtggatgg cgtcccatcc     180
cgcttcagcg gcagtggctc tggcacagat ttcactctca ccatcagcag cctgcagcct     240
gaagattttg caacttatta ctgcgttcag tatgatgagt ttccgtacgg tttcggcggc     300
ggcaccaagg tggagatcaa a                                              321

<210> SEQ ID NO 62
<211> LENGTH: 321
```

```
<212> TYPE: DNA
<213> ORGANISM: HUMAN

<400> SEQUENCE: 62
gacatccaga tgacccagtc tccatcctcc ctgtctgcat ctgtgggcga ccgcgtcacc      60
atcacttgta agttcagtca ggacattgat cgcttcctga gctggtttca gcagaaacca    120
ggcaaagccc ctaagtccct gatctatcgc gtgaagcgcc tggtggatgg cgtcccatcc    180
cgcttcagcg gcagtggctc tggcacagat ttcactctca ccatcagcag cctgcagcct    240
gaagattttg caacttatta ctgcgttcag tatgatgagt ttccgtacac cttcggcggc    300
ggcaccaagg tggagatcaa a                                              321

<210> SEQ ID NO 63
<211> LENGTH: 321
<212> TYPE: DNA
<213> ORGANISM: HUMAN

<400> SEQUENCE: 63
gacatccaga tgacccagtc tccatcctcc ctgtctgcat ctgtgggcga ccgcgtcacc      60
atcacttgta agttcagtca ggacattgat cgcttcctga gctggtttca gcagaaacca    120
ggcaaagccc ctaagtccct gatctatcgc gtgaagcgcc tggtggatgg cgtcccatcc    180
cgcttcagcg gcagtggctc tggcacagat ttcactctca ccatcagcag cctgcagcct    240
gaagattttg caacttatta ctgcgttcag tatgatgagt ttccgtacac cttcggcggc    300
ggcaccaagg tggagatcaa a                                              321

<210> SEQ ID NO 64
<211> LENGTH: 321
<212> TYPE: DNA
<213> ORGANISM: HUMAN

<400> SEQUENCE: 64
gacatccaga tgacccagtc tccatcctcc ctgtctgcat ctgtgggcga ccgcgtcacc      60
atcacttgta aggcgagtca ggacattgat cgcttcctga gctggtttca gcagaaacca    120
ggcaaagccc ctaagtccct gatctatcgc gtgaagcgcc tggtggatgg cgtcccatcc    180
cgcttcagcg gcagtggctc tggcacagat ttcactctca ccatcagcag cctgcagcct    240
gaagattttg caacttatta ctgcgttcag tatgatgagt ttccgtacac cttcggcggc    300
ggcaccaagg tggagatcaa a                                              321

<210> SEQ ID NO 65
<211> LENGTH: 990
<212> TYPE: DNA
<213> ORGANISM: HUMAN

<400> SEQUENCE: 65
tccaccaagg gcccatcggt cttccccgcta gcaccctcct ccaagagcac ctctgggggc      60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tgagcccaaa    300
tcttgtgaca aaactcacac atgcccaccg tgcccagcac ctgaactcct ggggggaccg    360
tcagtcttcc tcttcccccc aaaacccaag gacaccctca tgatctcccg gacccctgag    420
```

-continued

| | |
|---|---|
| gtcacatgcg tggtggtgga cgtgagccac gaagaccctg aggtcaagtt caactggtac | 480 |
| gtggacggcg tggaggtgca taatgccaag acaaagccgc gggaggagca gtacaacagc | 540 |
| acgtaccgtg tggtcagcgt cctcaccgtc ctgcaccagg actggctgaa tggcaaggag | 600 |
| tacaagtgca aggtctccaa caaagccctc ccagccccca tcgagaaaac catctccaaa | 660 |
| gccaaagggc agccccgaga accacaggtg tacaccctgc ccccatcccg ggacgagctg | 720 |
| accaagaacc aggtcagcct gacctgcctg gtcaaaggct tctatcccag cgacatcgcc | 780 |
| gtggagtggg agagcaatgg gcagccggag aacaactaca agaccacgcc cccgtgctg | 840 |
| gactccgacg gctccttctt cctctatagc aagctcaccg tggacaagag caggtggcag | 900 |
| caggggaacg tcttctcatg ctccgtgatg catgaggctc tgcacaacca ctacacgcag | 960 |
| aagagcctct ccctgtctcc gggtaaatga | 990 |

<210> SEQ ID NO 66
<211> LENGTH: 952
<212> TYPE: DNA
<213> ORGANISM: HUMAN

<400> SEQUENCE: 66

| | |
|---|---|
| ctagcgccct gctccaggag cacctccgag agcacagccg ccctgggctg cctggtcaag | 60 |
| gactacttcc ccgaaccggt gacggtgtcg tggaactcag cgccctgac cagcggcgtg | 120 |
| cacaccttcc cggctgtcct acagtcctca ggactctact ccctcagcag cgtggtgacc | 180 |
| gtgccctcca gcagcttggg cacgaagacc tacacctgca acgtagatca caagcccagc | 240 |
| aacaccaagg tggacaagag agttgagtcc aaatatggtc ccccatgccc accctgccca | 300 |
| gcacctgagt tcctgggggg accatcagtc ttcctgttcc cccaaaacc caaggacact | 360 |
| ctcatgatct cccggacccc tgaggtcacg tgcgtggtgg tggacgtgag ccaggaagac | 420 |
| cccgaggtcc agttcaactg gtacgtggat ggcgtggagg tgcataatgc caagacaaag | 480 |
| ccgcgggagg agcagttcaa cagcacgtac cgtgtggtca gcgtcctcac cgtcctgcac | 540 |
| caggactggc tgaacggcaa ggagtacaag tgcaaggtct ccaacaaagg cctcccgtcc | 600 |
| tccatcgaga aaaccatctc caaagccaaa gggcagcccc gagagccaca ggtgtacacc | 660 |
| ctgcccccat cccaggagga gatgaccaag aaccaggtca gcctgacctg cctggtcaaa | 720 |
| ggcttctacc ccagcgacat cgccgtggag tgggagagca atgggcagcc ggagaacaac | 780 |
| tacaagacca cgcctcccgt gctggactcc gacggctcct tcttcctcta cagcaggcta | 840 |
| accgtggaca agagcaggtg gcaggagggg aatgtcttct catgctccgt gatgcatgag | 900 |
| gctctgcaca accactacac acagaagagc ctctcccctgt ctctgggtaa at | 952 |

<210> SEQ ID NO 67
<211> LENGTH: 324
<212> TYPE: DNA
<213> ORGANISM: HUMAN

<400> SEQUENCE: 67

| | |
|---|---|
| cgaactgtgg ctgcaccatc tgtcttcatc ttcccgccat ctgatgagca gttgaaatct | 60 |
| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg ctaa | 324 |

<210> SEQ ID NO 68
<211> LENGTH: 467
<212> TYPE: PRT
<213> ORGANISM: Artificial Sequence
<220> FEATURE:
<223> OTHER INFORMATION: Synthetic Construct

<400> SEQUENCE: 68

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ser Ser Val Lys Val Ser Cys Lys Ala Ser Gly Tyr Thr
        35                  40                  45

Phe Asp Arg Tyr Trp Ile Glu Trp Val Arg Gln Ala Pro Gly Gln Gly
    50                  55                  60

Leu Glu Trp Met Gly Glu Ile Leu Pro Gly Ser Gly Asp Ile Asn Tyr
65                  70                  75                  80

Asn Glu Lys Phe Lys Gly Arg Val Thr Ile Thr Ala Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg Met Tyr Tyr Asp Tyr Asp Gln Gly Phe Asp
        115                 120                 125

Leu Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365
```

```
-continued

Tyr Thr Leu Pro Pro Ser Gln Glu Met Thr Lys Asn Gln Val Ser
    370             375             380

Leu Thr Cys Leu Val Lys Gly Phe Tyr Pro Ser Asp Ile Ala Val Glu
385             390             395                 400

Trp Glu Ser Asn Gly Gln Pro Glu Asn Asn Tyr Lys Thr Thr Pro Pro
            405             410             415

Val Leu Asp Ser Asp Gly Ser Phe Phe Leu Tyr Ser Arg Leu Thr Val
            420             425             430

Asp Lys Ser Arg Trp Gln Glu Gly Asn Val Phe Ser Cys Ser Val Met
        435             440             445

His Glu Ala Leu His Asn His Tyr Thr Gln Lys Ser Leu Ser Leu Ser
    450             455             460

Leu Gly Lys
465
```

HUMANIZED ANTI-IL-1 BETA ANTIBODIES

This application is a divisional of U.S. Ser. No. 10/542,508, filed Jul. 15, 2005 which is a 371 of PCT/US2004/000019, filed Jan. 21, 2004, now U.S. Pat. No. 7,541,033.

BACKGROUND OF THE INVENTION

Interleukin-1β (IL-1β) is a proinflammatory cytokine. IL-1β over-production has been implicated in the pathogenesis of a variety of diseases such as rheumatoid arthritis and osteoarthritis. IL-1β has been shown to increase cell migration into the inflamed synovium of joints by the up-regulation of adhesion molecules, the stimulation of the production of prostaglandins and metalloproteinase, the inhibition of collagen and proteoglycan synthesis, and the stimulation of osteoclastic bone resorption. Because of these properties, IL-1β is one of the primary mediators of bone and cartilage destruction in arthritis. Thus, agents that reduce the activity of IL-1β represent possible treatments for diseases such as arthritis.

There are three members of the IL-1 gene family: IL-1α, IL-1β, and IL-1 receptor antagonist (IL-1ra). IL-1α and IL-1β are agonists of the IL-1 receptor whereas the IL-1ra is a specific receptor antagonist and thus, an endogenous competitive inhibitor of IL-1. Administration of recombinant IL-1ra to patients in clinical trials provided significant clinical improvements in patients with severe rheumatoid arthritis compared to placebo. Furthermore, administration of IL-1ra reduced the rate of progressive joint damage. However, the poor pharmacokinetic properties and the large dose that must be administered make recombinant IL-1ra a less than ideal therapeutic agent.

A high affinity neutralizing antibody to IL-1β would make a superior therapeutic agent. The typical long elimination half-lives of antibodies coupled with high affinity binding result in a therapeutic with a reduced dose and frequency compared with recombinant IL-1ra. Although numerous IL-1β antibodies have been described, it has been exceedingly difficult to identify monoclonal antibodies hating high affinity, high specificity, and potent neutralizing activity.

The present invention encompasses humanized IL-1β antibodies derived from a unique murine antibody directed against human IL-1β, Mu007 (see PCT/US02/21281). These antibodies are high affinity antibodies with improved stability that have potent IL-1β neutralizing activity and are highly specific for IL-1β.

SUMMARY OF THE INVENTION

This invention encompasses an isolated antibody, or an antigen-binding portion thereof, that specifically binds human IL-1β, wherein said antibody is comprised of a light chain and a heavy chain and wherein said light chain is further comprised of a light chain CDR1 selected from the group consisting of SEQ ID NOS: 1, 12, 22, 29, 31, 33, 37, or 39; a light chain CDR2; and, a light chain CDR3 selected from the group consisting of SEQ ID NOS: 3, 7, 13, 15, 17, 20, 25, 34, or 41; and, said heavy chain is further comprised of a heavy chain CDR1 selected from the group consisting of SEQ ID NOS: 4 or 10; a heavy chain CDR2 sequence selected from the group consisting of SEQ ID NOS: 5, 8, 16, 18, 21, 23, or 28; and a heavy chain CDR3 selected from the group consisting of SEQ ID NOS: 6, 9, 11, 14, 19, 24, 26, 27, 30, 32, 35, 36, 38, 40, or 42; provided that said antibody does not consist of a light chain CDR1 of SEQ ID NO: 1, a light chain CDR2 of SEQ ID NO:2, a light chain CDR3 of SEQ ID NO:3, a heavy chain CDR1 of SEQ ID NO:4, a heavy chain CDR2 of SEQ ID NO:5, and a heavy chain CDR3 of SEQ ID NO:6.

The invention includes antibodies that bind mature human IL-1β with a $K_d$ of $1\times10^{-11}$ M or less and dissociate from mature human IL-1β with a $k_{off}$ rate constant of $1\times10^{-3}$ s$^{-1}$ or less as determined by surface plasmon resonance (HBS-EP buffer, pH 7.4 at 25° C.), and neutralize human IL-1β activity in a standard T1165.17 proliferation assay.

The invention further provides antibodies, preferably humanized antibodies, or antigen-binding portions thereof, in which deamidation is eliminated at position 55 of the heavy chain complementarity determining region 2 (HCDR2; SEQ ID NO: 44) resulting in improved stability.

The invention includes humanized antibodies comprising a light chain variable framework of human origin and three CDRs and a heavy chain variable framework of human origin and three CDRs having amino acid sequences encoded by polynucleotide sequences that correspond to SEQ ID NOS: 55-64.

Additionally, the invention includes humanized antibodies comprising a light chain variable framework of human origin and three CDRs and a heavy chain variable framework of human origin and three CDRs having amino acid sequences that correspond to SEQ ID NOS: 48-54, and 68.

The invention includes isolated nucleic acids comprising polynucleotides that encode the antibodies described and claimed herein. The invention also encompasses host cells transfected with these polynucleotides that express the antibodies described and claimed herein.

The invention encompasses methods of treating rheumatoid arthritis and osteoarthritis which comprise administering to a subject an effective amount of an antibody described and claimed herein as well as a method of inhibiting the destruction of cartilage that occurs in subjects that are prone to or have arthritis.

The invention further encompasses methods of treating neuroinflammation associated with stroke and ischemic, excitotoxic, and traumatic head injury which comprise administering to a subject an effective amount of an antibody described and claimed herein.

The invention still further encompasses the use of an antibody for the manufacture of a medicament to treat a subject with rheumatoid arthritis, osteoarthritis, or to inhibit cartilage destruction in a subject in need thereof.

Finally, the invention further encompasses the use of an antibody for the manufacture of a medicament to treat a subject with neuroinflammation associated with stroke and ischemic, excitotoxic, and traumatic head injury.

DETAILED DESCRIPTION OF THE INVENTION

This invention encompasses isolated human antibodies, or antigen-binding portions thereof, comprised substantially of the complementarity determining regions (CDRs) of the Mu007 antibody (SEQ ID NOS: 1-6) but wherein the polypeptide structures contain one or more amino acid differences in one or more of the CDRs thereof. The framework and other portions of these antibodies may originate from a human germ line. The humanized versions of Mu007 bind to human IL-1β with high affinity, a slow off rate and have a high neutralizing capacity. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to inhibit human IL-1β activity are also encompassed by the invention.

In order that the present invention may be more readily understood, certain terms are first defined.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Light chains are classified as kappa and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 3 or more amino acids.

IgG antibodies are the most abundant immunoglobulin in serum. IgG also has the longest half-life in serum of any immunoglobulin. Unlike other immunoglobulins, IgG is efficiently recirculated following binding to FcRn. There are four IgG subclasses G1, G2, G3, and G4, each of which have different effector functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

The term "antigen-binding portion" of an antibody (or simply "antibody portion"), as used herein, refers to one or more fragments of an antibody that retain the ability to specifically bind to an antigen (e.g., human IL-1β). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH I domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341: 544-546), which consists of a VH domain; and (vi) an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426: and Huston et al. (1988) Proc. Natl. Acad. Sci. USA 85: 5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6: 93-101) and use of a cysteine residue, a marker peptide and a C-terminal polyhistidine tag to make bivalent and biotinylated scFv molecules (Kipriyanov, S. M., et al. (1994) Mol. Immunol. 31: 1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "humanized antibody" means an antibody that is composed partially or fully of amino acid sequences derived from a human antibody germline or a rearranged sequence and made by altering the sequence of an antibody having non-human complementarity determining regions (CDR). The framework regions of the variable regions are substituted by corresponding human framework regions. As discussed herein, antibody in the context of humanized antibody is not limited to a full-length antibody and can include fragments and single chain forms.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucleic Acids Res. 20: 6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds human IL-1β is substantially free of antibodies that specifically bind antigens other than human IL-1β). An isolated antibody that specifically binds human IL-1β may, however, have cross-reactivity to other antigens, such as IL-1β molecules from other species. Moreover, an isolated antibody may be substantially free of other cellular material and/or chemicals.

A "neutralizing antibody", as used herein (or an "antibody that neutralizes human IL-1β activity"), is intended to refer to an antibody whose binding to human IL-1β results in inhibition of the biological activity of human IL-1β. Measuring one or more indicators of IL-1β biological activity as determined using either the T 1165.17 cell bioassay or the human IL-1β neutralization protocol described herein can assess this inhibition of the biological activity of human IL-1β.

Antibodies that "specifically bind" mature human IL-1β include antibodies as defined above that bind the mature form of human IL-1β known in the art and do not bind mature human IL-1α. An antibody that specifically binds mature human IL-1β may show some cross-reactivity with mature IL-1β from other species.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jonsson, U., et al. (1993) Ann. Biol. Clin. 51: 19-26; Jonsson, U., et al. (1991) Biotechniques 11: 620-627; Johnsson, B., et al. (1995) J. Mol. Recognit. 8: 125-131; and Johnnson, B., et al. (1991) Anal. Biochem. 198: 268-277.

The term "$k_{on}$", as used herein is intended to refer to the association or on rate constant, or specific reaction rate, of the forward, or complex-forming, reaction, measured in units: $M^{-1} sec^{-1}$.

The term "$k_{off}$", as used herein, is intended to refer to the dissociation or off rate constant, or specific reaction rate, for dissociation of an antibody from the antibody/antigen complex, measured in units: $sec^{-1}$.

The term "$K_d$", as used herein, is intended to refer to the dissociation constant of a particular antibody-antigen interaction. It is calculated by the formula:

$$k_{off}/k_{on}=K_d$$

The antibodies of the present invention are high potency antibodies, generally exhibiting low $k_{off}$ values. For purposes of the present disclosure, the term "high potency" refers to a potency reflected by a low $IC_{50}$ (or effective concentration showing a reduction of 50% in $^3H$ thymidine incorporation in the below described bioassay). The antibodies according to the present invention may be neutralizing (causing destruction of the target species, such as a IL-1β). An antibody not neutralizing for one use may be neutralizing for a different use.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind human IL-1β is intended to refer to a nucleic acid molecule in which the nucleotide sequences encoding the antibody or antibody portion are free of other nucleotide sequences encoding antibodies or antibody portions that bind antigens other than human IL-1β, which other sequences may naturally flank the nucleic acid in human genomic DNA. Thus, for example, an isolated nucleic acid of the invention encoding a VH region of an anti-human IL-1β antibody contains no other sequences encoding other VH regions that bind antigens other than human IL-1β.

The term "deamidated or deamidation" refers to the degradation of Asn or Gln residues in a protein/peptide (Robinson, et al. (2001) Proc. Natl. Acad. Sci. USA 12409-12413). For example, the intramolecular pathway for asparagine deamidation is via intermediate succinimide formation, resulting in a mixture of aspartyl and isoaspartyl residues (Harris, et al. (2001) J. of Chromatography 752: 233-245). Deamidation may lead to a reduction of stability and/or the reduction or loss of activity of the protein. Deamidation can occur ex vivo during the preparation of the formulated therapeutic, negatively impacting the manufacturing and storage of the pharmaceutical agent. Moreover, the deamidation can occur in vivo affecting the antibody's efficacy and duration of action.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome.

The term "recombinant host cell" (or simply "host cell"), as used herein, is intended to refer to a cell into which a recombinant expression vector has been introduced.

It has been found that a deamidation site in the CDR2 region of the Mu007 heavy chain influences the biological properties of humanized antibodies that contain this CDR2 region (see U.S. provisional patent application 60/361,423). Analogs of humanized antibodies that slow down or eliminate deamidation result in an antibody with improved stability. Thus, the invention includes antibodies in which deamidation is eliminated at position Asn55 of the heavy chain complementarity determining region 2 (HCDR2) by site specific changes.

The preferred antibodies or antigen-binding portions thereof of the present invention generally exhibit improved affinity (low $K_d$ values) and have binding specificity and potency similar to that observed for Mu007 and in which deamidation is eliminated at position Asn55 of HCDR2. The properties that define the antibodies of the present invention reside primarily in the variable regions of the antibody, more specifically the CDR regions of the antibody.

The primary impetus for humanizing antibodies from another species is to reduce the possibility that the antibody causes an immune response when injected into a human patient as a therapeutic. The more human sequences that are employed in a humanized antibody, the lower the risk of immunogenicity. In addition, the injected humanized antibodies generally have a longer half-life in the circulation than injected non-human antibodies. Furthermore, if effector function is desired, because the effector portion is human, it may interact better with the other parts of the human immune system. Changes can be made to the sequences described herein as preferable heavy and light chain regions without significantly affecting the biological properties of the antibody. This is especially true for the antibody constant regions and parts of the variable regions that do not influence the ability of the CDRs to bind to IL-1β.

Furthermore, as discussed herein, human framework variable regions and variants thereof may be used in the present invention. However, regardless of the framework chosen, if reducing the risk of immunogenicity is a focus, the number of changes relative to the human framework chosen should be minimized.

The heavy and light chain variable region framework residues can be derived from the same or different human antibody sequences. The human antibody sequences can be the sequences of naturally occurring human antibodies or can be consensus sequences of several human antibodies. Preferred human framework sequences for the heavy chain variable region of the humanized antibodies of the present invention include the VH segment DP-5 (Tomlinson, et al. (1992) *J. Mol. Biol.* 227: 776-798) and the J segment JH4, JH1 or JH5 (Ravetch, et al. (1981) *Cell* 27: 583-591). The Vk segment L1 (Cox, et al. (1994) *Eur. J. Immunol.* 24: 827-836) and the J segment Jk4 (Hieter, et al. (1982) *J. Biol. Chem.* 10: 1516-1522) are preferred sequences to provide the framework for the humanized light chain variable region.

Preferred human heavy chain constant region polynucleotide sequences of the humanized antibodies of the present invention include the IgG1 constant region or the IgG4 constant region:

IgG1
[SEQ ID NO: 65]
tccaccaagggcccatcggtcttccccgctagcaccctcctccaagagcac ctctggggggcacagcggccctgggctgcctggtcaaggactacttccccg aaccggtgacggtgtcgtggaactcaggcgccctgaccagcggcgtgcac accttcccggctgtcctacagtcctcaggactctactccctcagcagcgt ggtgaccgtgccctccagcagcttgggcacccagacctacatctgcaacg tgaatcacaagcccagcaacaccaaggtggacaagaaagttgagcccaaa tcttgtgacaaaactcacacatgcccaccgtgcccagcacctgaactcct ggggggaccgtcagtcttcctcttccccccaaaacccaaggacaccctca tgatctcccggacccctgaggtcacatgcgtggtggtggacgtgagccac gaagaccctgaggtcaagttcaactggtacgtggacggcgtggaggtgca taatgccaagacaaagccgcgggaggagcagtacaacagcacgtaccgtg tggtcagcgtcctcaccgtcctgcaccaggactggctgaatggcaaggag tacaagtgcaaggtctccaacaaagccctcccagcccccatcgagaaaac catctccaaagccaaagggcagccccgagaaccacaggtgtacaccctgc ccccatcccgggacgagctgaccaagaaccaggtcagcctgacctgcctg gtcaaaggcttctatcccagcgacatcgccgtggagtgggagagcaatgg gcagccggagaacaactacaagaccacgccccccgtgctggactccgacg gctccttcttcctctatagcaagctcaccgtggacaagagcaggtggcag caggggaacgtcttctcatgctccgtgatgcatgaggctctgcacaacca ctacacgcagaagagcctctccctgtctccgggtaaatga IgG4
[SEQ ID NO: 66]
ctagcgccctgctccaggagcacctccgagagcacagccgccctgggctg cctggtcaaggactacttccccgaaccggtgacggtgtcgtggaactcag gcgccctgaccagcggcgtgcacaccttcccggctgtcctacagtcctca ggactctactccctcagcagcgtggtgaccgtgccctccagcagcttggg cacgaagacctacacctgcaacgtagatcacaagcccagcaacaccaagg tggacaagagagttgagtccaaatatggtcccccatgcccaccctgccca gcacctgagttcctggggggaccatcagtcttcctgttccccccaaaacc -continued caaggacactctcatgatctcccggacccctgaggtcacgtgcgtggtgg tggacgtgagccaggaagaccccgaggtccagttcaactggtacgtggat ggcgtggaggtgcataatgccaagacaaagccgcgggaggagcagttcaa cagcacgtaccgtgtggtcagcgtcctcaccgtcctgcaccaggactggc tgaacggcaaggagtacaagtgcaaggtctccaacaaaggcctcccgtcc tccatcgagaaaaccatctccaaagccaaagggcagccccgagagccaca ggtgtacaccctgcccccatcccaggaggagatgaccaagaaccaggtca gcctgacctgcctggtcaaaggcttctaccccagcgacatcgccgtggag tgggagagcaatgggcagccggagaacaactacaagaccacgcctcccgtg ctggactccgacggctccttcttcctctacagcaggctaaccgtggacaa gagcaggtggcaggaggggaatgtcttctcatgctccgtgatgcatgagg ctctgcacaaccactacacacagaagagcctctccctgtctctgggtaa at.

The preferred human light chain constant region polynucleotide sequence of the humanized antibodies of the present invention is the kappa chain constant region:

[SEQ ID NO: 67]
cgaactgtggctgcaccatctgtcttcatcttcccgccatctgatgagca gttgaaatctggaactgcctctgttgtgtgcctgctgaataacttctatc ccagagaggccaaagtacagtggaaggtggataacgccctccaatcggt aactcccaggagagtgtcacagagcaggacagcaaggacagcacctacag cctcagcagcaccctgacgctgagcaaagcagactacgagaaacacaaag tctacgcctgcgaagtcacccatcagggcctgagctcgcccgtcacaaag agcttcaacaggggagagtgctaa The preferred antibodies of the present invention contain the IgG1 heavy chain constant region [SEQ ID NO: 65] or the IgG4 heavy chain constant region [SEQ ID NO:66] and the kappa light chain constant region [SEQ ID NO: 67], and are designated by the clone specified in Table 2 (i.e., W13, W17, etc.). The variable region polynucleotide sequences for the antibodies W13, W17, W18, W20, and U43, of the present invention include:

W13-Heavy Chain
[SEQ ID NO: 55]
ggatccactggtcaggtgcagctggtgcagtctggcgctgaggtgaagaa gcctggctcctccgtgaaggtctcctgcaaggcttctggctacacattcg accgctattggatcgagtgggtgcgccaggcccctggccaaggcctggag tggatgggcgagattctgcctggcagcggcgacattaactacaatgagaa gttcaagggccgcgtcacgattaccgcggacaaatccacgagcacagcct acatggagctgagcagcctgcgctctgaggacacggccgtgtattactgt gcgcgcatgtactatgattacgaccagggctttgactactggggccaggg caccctggtcaccgtctcctccgcctccaccaagggcccatcggtcttcc cgctagc W13-Light Chain

[SEQ ID NO: 60]

gacatccagatgacccagtctccatcctccctgtctgcatctgtgggcga
ccgcgtcaccatcacttgtaagttcagtcaggacattgatcgcttcctga
cctggtttcagcagaaaccaggcaaagcccctaagtccctgatctatcgc
gtgaagcgcctggtggatggcgtcccatcccgcttcagcggcagtggctc
tggcacagatttcactctcaccatcagcagcctgcagcctgaagattttg
caacttattactgcatccagtatgatgagtttccgtacaccttcggcggc
ggcaccaaggtggagatcaaa W17-Heavy Chain

[SEQ ID NO: 56]

ggatccactggtcaggtgcagctggtgcagtctggcgctgaggtgaagaa
gcctggctcctccgtgaaggtctcctgcaaggcttctggctacacattcg
accgctattggatcgagtgggtgcgccaggcccctggccaaggcctggag
tggatgggcgagattctgcctggcagcggcgacattaactacaatgagaa
gttcaagggccgcgtcacgattaccgcggacaaatccacgagcacagcct
acatggagctggagcagcctgcgctctgaggacacggccgtgtattactg
tgcgcgcatgtactatgattacgaccaggctttgacctgtggggccaggg
caccctggtcaccgtctcctccgcctccaccaagggcccatcggtcttc
ccgctagc W17-Light Chain

[SEQ ID NO: 61]

gacatccagatgacccagtctccatcctccctgtctgcatctgtgggcga
ccgcgtcaccatcacttgtaagttcagtcaggacattgatcgcttcctga
gctggtttcagcagaaaccaggcaaagcccctaagtccctgatctatcgc
gtgaagcgcctggtggatggcgtcccatcccgcttcagcggcagtggctc
tggcacagatttcactctcaccatcagcagcctgcagcctgaagattttg
caacttattactgcgttcagtatgatgagtttccgtacggttttcggcggc
ggcaccaaggtggagatcaaa W18-Heavy Chain

[SEQ ID NO: 57]

ggatccactggtcaggtgcagctggtgcagtctggcgctgaggtgaagaa
gcctggctcctccgtgaaggtctcctgcaaggcttctggctacacattcg
accgctattggatcgagtgggtgcgccaggcccctggccaaggcctggag
tggatgggcgagattctgcctggcagcggcaccattaactacaatgagaa
gttcaagggccgcgtcacgattaccgcggacaaatccacgagcacagcct
acatggagctgagcagcctgcgctctgaggacacffxxfrfrattactgt
gcgcgcatgtactatgattacgaccagggctttgacaactggggccaggg
caccctggtcaccgtctcctccgcctccaccaagggcccatcggtcttcc
cgctagc W18-Light Chain

[SEQ ID NO: 62]

gacatccagatgacccagtctccatcctccctgtctgcatctgtgggcga
ccgcgtcaccatcacttgtaagttcagtcaggacattgatcgcttcctga
gctggtttcagcagaaaccaggcaaagcccctaagtccctgatctatcgc
gtgaagcgcctggtggatggcgtcccatcccgcttcagcggcagtggctc
tggcacagatttcactctcaccatcagcagcctgcagcctgaagattttg
caacttattactgcgttcagtatgatgagtttccgtacaccttcggcggc
ggcaccaaggtggagatcaaa W20-Heavy Chain

[SEQ ID NO: 59]

ggatccactgtcaggtgcagctggtgcagtctggcgctgaggtgaagaag
cctggctcctccgtgaaggtctcctgcaaggcttctggctacacattcga
ccgctattggatcgatgggtgcgccaggcccctggccaaggcctggagtg
gatgggcgagattctgcctggcagcggcgacattaactacaatgagaagt
tcaaggccgcgtcacgattaccgcggacaaatccacgagcacagcctac
atggagctgagcagcctgcgctctgaggacacggccgtgtattactgtgc
gcgcatgtactatgattacgaccaggctttgactactggggccagggca
ccctggtcaccgtctcctccgcctccaccaagggcccatcggtcttcccg
ctagc W20-Light Chain

[SEQ ID NO: 63]

gacatccagatgacccagtctccatcctccctgtctgcatctgtgggcga
ccgcgtcaccatcacttgtaagttcagtcaggacattgatcgcttcctga
gctggtttcagcagaaaccaggcaaagcccctaagtccctgatctatcgc
gtgaagcgcctggtggatggcgtcccatcccgcttcagcggcagtggctc
tggcacagatttcactctcaccatcagcagcctgcagcctgaagattttg
caacttattactgcgttcagtatgatgagtttccgtacaccttcggcggc
ggcaccaaggtggagatcaaa U43-Heavy Chain

[SEQ ID NO: 58]

ggatccactggtcaggtgcagctggtgcagtctggcgctgaggtgaagaa
gcctggctcctccgtgaaggtctcctgcaaggcttctggctacacattcg
accgctattggatcgagtgggtgcgccaggcccctggccaaggcctggag
tggatgggcgagattctgcctggcagcggcgacattaactacaatgagaa
gttcaagggccgcgtcacgattaccgcggacaaatccacgagcacagcct
acatggagctgagcagcctgcgctctgaggacacggccgtgtattactgt
gcgcgcatgtactatgattacgaccagggctttagcctgtggggccaggg
caccctggtcaccgtctcctccgcctccaccaagggcccatcggtcttcc
cgctagc U43-Light Chain

[SEQ ID NO: 64]

gacatccagatgacccagtctccatcctccctgtctgcatctgtgggcga
ccgcgtcaccatcacttgtaaggcgagtcaggacattgatcgcttcctga
gctggtttcagcagaaaccaggcaaagcccctaagtccctgatctatcgc
gtgaagcgcctggtggatggcgtcccatcccgcttcagcggcagtggctc
tggcacagatttcactctcaccatcagcagcctgcagcctgaagattttg
caacttattactgcgttcagtatgatgagtttccgtacaccttcggcggc
ggcaccaaggtggagatcaaa In another embodiment, the mature amino acid sequences of the antibodies of the present invention, W13, W17, W18, W20, and U43, include:

```
W13-Heavy Chain
                                            [SEQ ID NO: 45]
QVQLVQSGAE VKKPGSSVKV SCKASGYTFD RYWIEWVRQA
PGQGLEWMGE ILPGSGDINY NEKFKGRVTI TADKSTSTAY
MELSSLRSED TAVYYCARMY YDYDQGFDYW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSCDKTHTCP PCPAPELLGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSRDE
LTKNQVSLTC LVKGFYPSDI AVEWESNGQP ENNYKTTPPV
LDSDGSFFLY SKLTVDKSRW QQGNVFSCSV MHEALHNHYT
QKSLSLSPGK W13-Light Chain
                                            [SEQ ID NO: 46]
DIQMTQSPSS LSASVGDRVT ITCKFSQDID RFLTWFQQKP
GKAPKSLIYR VKRLVDGVPS RFSGSGSGTD FTLTISSLQP
EDFATYYCIQ YDEFPYTFGG GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC W17-IgG1 Heavy Chain
                                            [SEQ ID NO: 47]
QVQLVQSGAE VKKPGSSVKV SCKASGYTFD RYWIEWVRQA
PGQGLEWMGE ILPGSGDINY NEKFKGRVTI TADKSTSTAY
MELSSLRSED TAVYYCARMY YDYDQGFDLW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNYNHKPS NTKVDKKVEP KSCDKTHTCP PCPAPELLGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSRDE
LTKNQVSLTC LVKGFYPSDI AVEWESNGQP ENNYKTTPPV
LDSDGSFFLY SKLTVDKSRW QQGNVFSCSV MHEALHNHYT
QKSLSLSPGK W17-IgG4 Heavy Chain
                                            [SEQ ID NO: 68]
QVQLVQSGAEVKKPGSSVKVSCKASGYTFDRYWIEWVRQAPGQGLEWMGE
ILPGSGDINYNEKFKGRVTITADKSTSTAYMELSSLRSEDTAVYYCARMY
YDYDQGFDLWGQGTLVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKLPSNTKVDKRVESKYGPPCPPCPAPEFLGGPSVFLFPPKPKD
TLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK W17-Light Chain
                                            [SEQ ID NO: 48]
DIQMTQSPSS LSASVGDRVT ITCKFSQDID RFLSWFQQKP
GKAPKSLIYR VKRLVDGVPS RFSGSGSGTD FTLTISSLQP
EDFATYYCVQ YDEFPYGFGG GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC W18-Heavy Chain
                                            [SEQ ID NO: 49]
QVQLVQSGAE VKKPGSSVKV SCKASGYTFD RYWIEWVRQA
PGQGLEWMGE ILPGSGTINY NEKFKGRVTI TADKSTSTAY
MELSSLRSED TAVYYCARMY YDYDQGFDNW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSCDKTHTCP PCPAPELLGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSRDE
LTKNQVSLTC LVKGFYPSDI AVEWESNGQP ENNYKTTPPV
LDSDGSFFLY SKLTVDKSRW QQGNVFSCSV MHEALHNHYT
QKSLSLSPGK W18-Light Chain
                                            [SEQ ID NO: 50]
DIQMTQSPSS LSASVGDRVT ITCKFSQDID RFLSWFQQKP
GKAPKSLIYR VKRLVDGVPS RFSGSGSGTD FTLTISSLQP
EDFATYYCVQ YDEFPYTFGG GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGE W20-Heavy Chain
                                            [SEQ ID NO: 51]
QVQLVQSGAE VKKPGSSVKV SCKASGYTFD RYWIEWVRQA
PGQGLEWMGE ILPGSGDINY NEKFKGRVTI TADKSTSTAY
MELSSLRSED TAVYYCARMY YDYDQGFDYW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSCDKTHTCP PCPAPELLGG
PSVFLFPPKP KDTLMISRTP EVTCVVVDVS HEDPEVKFNW
```

-continued

```
YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK

W20-Light Chain
                                     [SEQ ID NO: 52]
DIQMTQSPSS LSASVGDRVT ITCKFSQDID RFLSWFQQKP

GKAPKSLIYR VKRLVDGVPS RFSGSGSGTD FTLTISSLQP

EDFATYYCVQ YDEFPYTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC

U43 Heavy Chain
                                     [SEQ ID NO: 53]
QVQLVQSGAE VKKPGSSVKV SCKASGYTFD RYWIEWVRQA

PGQGLEWMGE ILPGSGDINY NEKFKGRVTI TADKSTSTAY

MELSSLRSED TAVYYCARMY YDYDQGFSLW GQGTLVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPEEPQ VYTLPPSRDE

LTKNQVSLTC LVKGPYPSDI AVEWESNGQP ENNYKTTPPV

LDSDGSFFLY SKLTVDKSRW QQGNVFSCSV MHEALHNHYT

QKSLSLSPGK

U43-Light chain
                                     [SEQ ID NO: 54]
DIQMTQSPSS LSASVGDRVT ITCKASQDID RFLSWFQQKP

GKAPKSLIYR VKRLVDGVPS RFSGSGSGTD FTLTISSLQP

EDFATYYCVQ YDEFPYTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The present invention encompasses antibodies or antigen-binding portions thereof that make use of one or more of light chain CDR1, CDR2, or CDR3, or heavy chain CDR1, [SEQ ID NOS: 1-4], of antibody Mu007. The CDRs encompassed by the present invention are the hypervariable regions of the Mu007 antibody that provide the majority of contact residues for the binding of the antibody to a specific IL-1β epitope. Thus, the CDRs described herein can be used to make full-length antibodies as well as functional fragments and analogs or other proteins which when attached to the CDRs maintain the CDRs in an active structural conformation such that the binding affinity of the protein employing the CDRs is specific for mature IL-1β.

The binding affinity of the Mu007 antibody was determined using surface plasmon resonance (BIAcore™) [see Example 1]. In these experiments the antibody was captured at low density by either protein A or anti-Fc antibody on a BIAcore™ chip and ligand was flowed past. Build up of mass at the surface of the chip was measured. This analytical method allows the determination in real time of both on and off rates to obtain affinity ($K_d$) for binding. The Mu007 antibody has a $K_d$ of approximately 6.2 pM (picomolar). Preferred humanized antibodies of the present invention, i.e., W13, W17, W18, W20, and U43, had $K_d$'s of approximately 2.8 pM, 2.8 pM, 4.2 pM, 2.7 pM, and 4.7 pM respectively (see Example 1, Table 3).

It is also preferred that the antibodies or antigen-binding portions thereof of the present invention bind specifically to IL-1β and not other IL-1 family members or structurally related proteins within the same species.

It is also preferred that the antibodies or antigen-binding portions thereof of the present invention neutralize the biological activity of IL-1β. Two different assays were utilized to test the ability of Mu007 and preferred antibodies of the present invention to neutralize IL-1β activity [see Examples 2 and 3].

A murine cell line, T1165.17, that requires low levels of IL-1β for proliferation was used in the first assay. Human IL-1β was present at a constant level in the medium and a dilution series of each antibody was added. Inhibition of proliferation provided a measurement of the antibody's ability to block IL-1β activation of the IL-1 receptor. Proliferation measurements for different concentrations of antibody resulted in an average $IC_{50}$ value of 20.6 pM for Mu007 and 1.2 pM for W13, 1.8 pM for W17, 2.0 pM for W18, and 4.0 pM for U43 respectively (See Example 2, Table 4).

It is preferred that the antibodies or antigen-binding portions thereof of the present invention have an $IC_{50}$ value that is lower than that of Mu007. "$IC_{50}$" as referred to herein is the measure of potency of an antibody to inhibit the activity of human IL-1β. $IC_{50}$ is the concentration of antibody that results in 50% IL-1β inhibition in a single dose experiment. The $IC_{50}$ can be measured by any assay that detects inhibition of human IL-1β activity. However, the $IC_{50}$ values obtained may vary depending on the assay used. There may even be some variability between experiments using the same assay. For example, the condition of the IL-1β dependent cells discussed herein, has an effect on the $IC_{50}$ values obtained. Thus, the critical value for the purposes of the present invention is a value relative to that obtained using Mu007 or the preferred antibodies of the present invention in a single experiment.

The second assay utilized is an IL-6 neutralization assay. Neither Mu007 nor the preferred antibodies of the present invention cross-react with mouse IL-1β making it difficult to use a mouse model to test neutralizing activity in vivo.

However, one consequence of the proinflammatory activity of IL-1β is the induction of IL-6, another proinflammatory cytokine that mediates some of the non-local effects of IL-1β. Human IL-1β is able to bind and stimulate the mouse IL-1β receptor, leading to an elevation of mouse IL-6. Thus, an antibody with neutralizing activity would block the induction of IL-6 in a mouse given a dose of human IL-1β. Both Mu007 and the antibodies of the present invention demonstrated potent neutralization of human IL-1β in the murine model of inflammatory stimulation (See Example 3).

The present invention also is directed to recombinant DNA encoding antibodies which, when expressed, specifically bind to human IL-1β. Preferably, the DNA encodes antibodies that, when expressed, comprise one or more of the heavy and light chain CDRs of Mu007 [SEQ ID NOS: 1-6], and one or more of the heavy and light chain CDRs of the present invention [SEQ ID NOS: 7-42]. Exemplary DNA sequences which, on expression, code for the polypeptide chains comprising the heavy chain variable regions of the preferred antibodies of the present invention are represented as SEQ ID NOS: 55-59. Exemplary DNA sequences which, on expression, code for the polypeptide chains comprising the light chain variable regions of the preferred antibodies of the present invention are represented as SEQ ID NOS: 60-64.

The neutralizing antibodies of the present invention are achieved through generating appropriate antibody gene sequences, i.e., amino acid sequences, by arranging the appropriate nucleotide sequences and expressing these in a suitable cell line. Any desired nucleotide sequences can be produced using the method of codon based mutagenesis, as described, for example, in U.S. Pat. Nos. 5,264,563 and 5,523,388. Such procedures permit the production of any and all frequencies of amino acid residues at any desired codon positions within an oligonucleotide. This can include completely random substitutions of any of the 20 amino acids at a desired position. Alternatively, this process can be carried out so as to achieve a particular amino acid at a desired location within an amino acid chain, such as the novel CDR sequences according to the invention. In sum, the appropriate nucleotide sequence to express any amino acid sequence desired can be readily achieved and using such procedures the novel CDR sequences of the present invention can be reproduced. This results in the ability to synthesize polypeptides, such as antibodies, with any desired amino acid sequences. For example, it is now possible to determine the amino acid sequences of any desired domains of an antibody of choice and, optionally, to prepare homologous chains with one or more amino acids replaced by other desired amino acids, so as to give a range of substituted analogs.

In applying such methods, it is to be appreciated that due to the degeneracy of the genetic code, such methods as random oligonucleotide synthesis and partial degenerate oligonucleotide synthesis will incorporate redundancies for codons specifying a particular amino acid residue at a particular position, although such methods can be used to provide a master set of all possible amino acid sequences and screen these for optimal function as antibody structures or for other purposes. Such methods are described in Cwirla et al, Proc. Natl. Acad. Sci. 87: 6378-6382 (1990) and Devlin et al., Science 249: 404-406 (1990). Alternatively, such antibody sequences can be synthesized chemically or generated in other ways well known to those skilled in the art.

In accordance with the invention disclosed herein, enhanced high potency antibodies can be generated by combining in a single polypeptide structure one or more novel CDR sequences as disclosed herein, each shown to independently result in enhanced potency or biological activity and reduced deamidation. In this manner, several novel amino acid sequences can be combined into one antibody, in the same or different CDRs, to produce antibodies with desirable levels of biological activity. Such desirable levels will often result from producing antibodies whose $k_{off}$ values are at preferably less than $10^{-3}$ $s^{-1}$, more preferably less than $5\times10^{-4}$ $s^{-1}$, and even more preferably less than $1\times10^{-4}$ $s^{-1}$. By way of a non-limiting example, 36 such novel CDR sequences [SEQ ID NOS: 7-42] may be employed and the resulting antibodies screened for potency, or biological activity, using either the T1165.17 cell bioassay or the human IL-1β neutralization protocol described herein, where the antibody demonstrates high affinity for a particular antigenic structure, such as human IL-1β. The overall result would thus be an iterative process of combining various single amino acid substitutions and screening the resulting antibodies for antigenic affinity and potency in a step-by-step manner, thereby insuring that potency is increased without sacrifice of a desirably high, or at least minimum value for, affinity. This iterative method can be used to generate double and triple amino acid replacements in a stepwise process so as to narrow the search for antibodies having higher affinity (see WO 01/64751 and US 2002/0098189). Consequently, the amino acids of each CDR region of the Mu007 antibody were systematically substituted and the resulting antibodies were screened for antigenic affinity. It was determined that amino acid substitutions at any position in the light chain CDR2 did not result, in general, in an increase in antibody affinity. Thus, a light chain CDR2 of the present invention is preferably Mu007 light chain CDR2 sequence [SEQ ID NO:2] since amino acid substitutions in this CDR did not result in antibodies of higher affinity.

Conversely, it must be appreciated that not all locations within the sequences of the different antibody domains may be equal in that substitutions of any kind in a particular location may be helpful or detrimental. In addition, substitutions of certain kinds of amino acids at certain locations may likewise be a plus or a minus regarding affinity. For example, it may not be necessary to try all possible hydrophobic amino acids at a given position. It may be that any hydrophobic amino acid will do as well. On the other hand, an acidic or basic amino acid at a given location may provide large swings in measured affinity.

As already described, $K_d$ is measured by the ratio of the $k_{on}$ and $k_{off}$ constants. For example, a $k_{on}$ of $3.1\times10^7(M^{-1} s^{-1})$ and a $k_{off}$ of $0.9\times10^{-4}(s^{-1})$ would combine to give a $K_d$ of $2.9\times10^{-12}$ M. Thus, affinity can be improved by increasing the $k_{on}$ or decreasing the $k_{off}$. Accordingly, a decrease in the $k_{off}$ of antibodies of the present invention will likely result in a more efficacious therapeutic agent.

In accordance with the present invention, increased potency of an existing antibody, regardless of its antigen affinity, is achieved through selective changes to one or more of the amino acids present in one or more of the CDR regions of said antibody whereby said amino acid changes have the effect of producing a decrease in the $k_{off}$ for said antibody, preferably with an increase in antibody affinity. Higher potency can be achieved with a lower $k_{off}$ value even if the affinity remains the same or is reduced somewhat. Such an antibody is most advantageously produced by synthesis of the required polypeptide chains via synthesis in suitably engineered cells having incorporated therein the appropriate nucleotide sequences coding for the required polypeptide chains containing the altered CDR segments. Also in accordance with the present invention, a novel antibody having a desirable level of potency, or biological activity, can be prepared de novo by incorporation of selected amino acids at selected locations within the CDR regions of said antibody polypeptide chains using genetically engineered cells as described herein or wholly through chemical synthesis of the required polypeptide chains with subsequent formation of the necessary disulfide bonds.

In accordance with the foregoing, the antibodies of the present invention are high potency monoclonal antibodies. Such antibodies, however, are monoclonal only in the sense that they may be derived from a clone of a single cell type. However, this is not meant to limit them to a particular origin. Such antibodies may readily be produced in cells that commonly do not produce antibodies, such as CHO, NSO, or COS cells. In addition, such antibodies may be produced in other types of cells, especially mammalian and even plant cells, by genetically engineering such cells to express and assemble the polypeptide light and heavy chains forming the antibody product. In addition, such chains can be chemically synthesized but, since they would be specific for a given antigenic determinant, would still constitute "monoclonal" antibodies within the spirit in which that term is used. Thus, as used herein, the term monoclonal antibody is intended to denote more the specificity and purity of the antibody molecules rather than the mere mechanism used for production of said antibodies.

Also as used herein, the term potency is intended to describe the dependency of the effect of the antibody, when utilized for its intended therapeutic purpose, on the concentration of such antibody. Thus, potency means biological activity with respect to a given antigen. By way of non-limiting example, the potency, or biological activity, or biological effect, is measured for an anti-IL-1β antibody, by either the T1165.17 cell bioassay or the human IL-1β neutralization protocol, as described herein. Conversely, the affinity of an antibody for the antigen is simply a mathematical measure of the ratio of $k_{on}$ to $k_{off}$. In addition, the $K_d$ of the antibodies produced according to the methods of the present invention will typically be in the range of $10^{-12}$ M or less.

In one embodiment, the antibodies or antigen-binding portions thereof of the present invention will commonly comprise a mammalian, preferably a human, constant region and a variable region, said variable region comprising heavy and light chain framework regions and heavy and light chain CDRs, wherein the heavy and light chain framework regions have sequences characteristic of a mammalian antibody, preferably a human antibody, and wherein the CDR sequences are similar to those of an antibody of some species other than a human, preferably a mouse. The CDR sequences of Mu007 are as shown in Table 1.

TABLE 1

Basic CDR sequences as provided in SEQ ID NOS: 43 and 44

| CDR | Sequence | SEQ ID NO. |
|---|---|---|
| L1 | KASQDIDRYLS | 1 |
| L2 | RVKRLVD | 2 |
| L3 | LQYDEFPYT | 3 |
| H1 | GYTFSRYWIE | 4 |
| H2 | EILPGNGNINYNEKFKG | 5 |
| H3 | IYYDYDQGFTY | 6 |

In keeping with the foregoing, and in order to better describe the sequences disclosed according to the invention with respect to a humanized antibody against human IL-1β, a basic or starting sequence of light and heavy chain variable regions of Mu007 are shown in the light chain variable region—SEQ ID NO: 43, and the heavy chain variable region—SEQ ID NO: 44. Also in accordance with the inventions specific amino acids different from these starting sequences were generated by recombinant methods starting with prepared nucleotide sequences designed to generate said amino acid sequences when expressed in recombinant cells. The products of said cells are the monoclonal antibodies of the present invention provided that no antibody has the combination of SEQ ID NO: 1 for CDR L1, SEQ ID NO:2 for CDR L2, SEQ ID NO:3 for CDR L3, SEQ ID NO:4 for CDR H1, SEQ ID NO:5 for CDR H2, and SEQ ID NO:6 for CDR H3.

In one embodiment of the present invention, potency is increased using a neutralizing antibody Fab fragment against human IL-1β having a $K_d$ of at least $10^{-11}$ M, and preferably at least $10^{-12}$ M by decreasing the $k_{off}$ value to at least $10^{-3}$ s$^{-1}$, preferably at least $5\times10^{-4}$ s$^{-1}$, more preferably at least $10^{-4}$ s$^{-1}$. The amino acids present in the CDRs of such Fab fragments are shown in Table 2.

Table 2 indicates the amino acid sequences (all sequences in standard amino acid one letter code) of the CDRs employed in the antibodies of the present invention. In Table 2, the locations of key amino acid substitutions made in the corresponding CDRs of Table 1 (i.e., locations at which CDRs differ in amino acids) are indicated in bold face and underlined. The Fab fragments were initially screened by a standard ELISA. IC$_{50}$ values measured by the T1165.17 cell proliferation assay are indicated as a comparison of the recombinantly produced Fab variants with a wild type control (wt/Fab). The Fab variants and subsequent antibodies of the present invention are referred to by their clone designations from Table 2.

TABLE 2

Sequences of CDRs tending to induce high potency in antibodies

| Clone | CDR | Sequence | SEQ ID NO. | IC$_{50}$ wt/Fab |
|---|---|---|---|---|
| U2 | L1 | KASQDIDRYLS | 1 | 3 |
|  | L2 | RVKRLVD | 2 |  |
|  | L3 | VQYDEFNYT | 7 |  |
|  | H1 | GYTFSRYWIE | 4 |  |
|  | H2 | EILPGTGTINYNEKFKG | 8 |  |
|  | H3 | VYYDYDYGFDY | 9 |  |
| U3 | L1 | KASQDIDRYLS | 1 | 3 |
|  | L2 | RVKRLVD | 2 |  |
|  | L3 | VQYDEFNYT | 7 |  |
|  | H1 | GYTFDRYWIE | 10 |  |
|  | H2 | EILPGTGTINYNEKFKG | 8 |  |
|  | H3 | VYYDYDYGFDL | 11 |  |
| U4 | L1 | KASQDIDRYLT | 12 | 2 |
|  | L2 | RVKRLVD | 2 |  |
|  | L3 | VQYDEFNYT | 7 |  |
|  | H1 | GYTFDRYWIE | 10 |  |
|  | H2 | EILPGTGTINYNEKFKG | 8 |  |
|  | H3 | VYYDYDYGFDL | 11 |  |
| U5 | L1 | KASQDIDRYLT | 12 | 0.5 |
|  | L2 | RVKRLVD | 2 |  |
|  | L3 | IQYDEFNYT | 13 |  |
|  | H1 | GYTFSRYWIE | 4 |  |

TABLE 2-continued

Sequences of CDRs tending to induce high potency in antibodies

| Clone | CDR | Sequence | SEQ ID NO. | IC$_{50}$ wt/Fab |
|---|---|---|---|---|
| U6 | H2 | EILPGTGTINYNEKFKG | 8 | |
| | H3 | VYYDYYGFDN | 14 | |
| | L1 | KASQDIDRYLT | 12 | 3 |
| | L2 | RVKRLVD | 2 | |
| | L3 | VQYDEFNYT | 7 | |
| U7 | H1 | GYTFDRYWIE | 10 | |
| | H2 | EILPGTGTINYNEKFKG | 8 | |
| | H3 | VYYDYYGFDN | 14 | |
| | L1 | KASQDIDRYLT | 12 | 2 |
| | L2 | RVKRLVD | 2 | |
| | L3 | VQYDEFNYT | 7 | |
| U8 | H1 | GYTFDRYWIE | 10 | |
| | H2 | EILPGTGTINYNEKFKG | 8 | |
| | H3 | VYYDYYGFDN | 14 | |
| | L1 | KASQDIDRYLT | 12 | 2 |
| | L2 | RVKRLVD | 2 | |
| | L3 | IQYDEFPYT | 15 | |
| U9 | H1 | GYTFDRYWIE | 10 | |
| | H2 | EILPGSGTINYNEKFKG | 16 | |
| | H3 | VYYDYYGFDN | 14 | |
| | L1 | KASQDIDRYLS | 1 | 2 |
| | L2 | RVKRLVD | 2 | |
| | L3 | VQYDEFPYT | 17 | |
| U10 | H1 | GYTFDRYWIE | 10 | |
| | H2 | EILPGTGD**INYNEKFKG | 18 | |
| | H3 | VYYDYYGFTL | 19 | |
| | L1 | KASQDIDRYLS | 1 | 0.5 |
| | L2 | RVKRLVD | 2 | |
| | L3 | VQYDEFPYT | 17 | |
| U11 | H1 | GYTFSRYWIE | 4 | |
| | H2 | EILPGTGTINYNEKFKG | 8 | |
| | H3 | VYYDYYGFDN | 14 | |
| | L1 | KASQDIDRYLS | 1 | 2 |
| | L2 | RVKRLVD | 2 | |
| | L3 | IQYDEFPYL | 20 | |
| | H1 | GYTFDRYWIE | 10 | |
| U12 | H2 | EILPGTGTINYNEKFKG | 8 | |
| | H3 | VYYDYYGFDN | 14 | |
| | L1 | KASQDIDRYLS | 1 | 5 |
| | L2 | RVKRLVD | 2 | |
| | L3 | IQYDEFPYL | 20 | |
| U13 | H1 | GYTFDRYWIE | 10 | |
| | H2 | EILPGTGTINYNEKFKG | 8 | |
| | H3 | VYYDYYGFDN | 14 | |
| | L1 | KASQDIDRYLS | 1 | 4 |
| | L2 | RVKRLVD | 2 | |
| | L3 | IQYDEFNYT | 13 | |
| U14 | H1 | GYTFDRYWIE | 10 | |
| | H2 | EILPGSGD**INYNEKFKG | 21 | |
| | H3 | VYYDYYGFDN | 14 | |
| | L1 | KASQDIDRYLS | 1 | 3 |
| | L2 | RVKRLVD | 2 | |
| | L3 | IQYDEFNYT | 13 | |
| U15 | H1 | GYTFDRYWIE | 10 | |
| | H2 | EILPGSGD**INYNEKFKG | 21 | |
| | H3 | VYYDYYGFDN | 14 | |
| | L1 | KASQDIDRYLT | 12 | 2 |
| | L2 | RVKRLVD | 2 | |
| | L3 | IQYDEEPYT | 15 | |
| U16 | H1 | GYTFDRYWIE | 10 | |
| | H2 | EILPGTGTINYNEKFKG | 8 | |
| | H3 | VYYDYYGFDY | 9 | |
| | L1 | KASQDIDRYLT | 12 | 0.5 |
| | L2 | RVKRLVD | 2 | |
| | L3 | IQYDEFNYT | 13 | |
| U17 | H1 | GYTFSRYWIE | 4 | |
| | H2 | EILPGSGTINYNEKFKG | 16 | |
| | H3 | VYYDYYGFDN | 14 | |
| | L1 | KASQDIDRYLT | 12 | 1 |
| | L2 | RVKRLVD | 2 | |
| | L3 | IQYDEFPYT | 15 | |
| | H1 | GYTFDRYWIE | 10 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
| | H2 | EILPGTGTINYNEKFKG | 8 | |
| | H3 | VYYDYDYGFDY | 9 | |
| U18 | L1 | KASQDIDRYLT | 12 | 2 |
| | L2 | RVKRLVD | 2 | |
| | L3 | IQYDEFNYT | 13 | |
| | H1 | GYTFSRYWIE | 4 | |
| | H2 | EILPGSGTINYNEKFKG | 16 | |
| | H3 | VYYDYDYGFDN | 14 | |
| U19 | L1 | KASQDIDRYLT | 12 | 2 |
| | L2 | RVKRLVD | 2 | |
| | L3 | VQYDEFPYT | 17 | |
| | H1 | GYTFSRYWIE | 4 | |
| | H2 | EILPGTGDINYNEKFKG | 18 | |
| | H3 | VYYDYDYGFDN | 14 | |
| U20 | L1 | KASQDIDRYLS | 1 | 2 |
| | L2 | RVKRLVD | 2 | |
| | L3 | VQYDEFPYT | 17 | |
| | H1 | GYTFSRYWIE | 4 | |
| | H2 | EILPGSGDINYNEKFKG | 21 | |
| | H3 | VYYDYDYGFDY | 9 | |
| U21 | L1 | KASQDIDRYLT | 12 | 2 |
| | L2 | RVKRLVD | 2 | |
| | L3 | VQYDEFPYT | 17 | |
| | H1 | GYTFSRYWIE | 4 | |
| | H2 | EILPGTGDINYNEKFKG | 18 | |
| | H3 | VYYDYDYGFDN | 14 | |
| U22 | L1 | KASQDIDRYLS | 1 | 2 |
| | L2 | RVKRLVD | 2 | |
| | L3 | IQYDEFNYT | 13 | |
| | H1 | GYTFDRYWIE | 10 | |
| | H2 | EILPGTGTINYNEKFKG | 8 | |
| | H3 | VYYDYDYGFDY | 9 | |
| U23 | L1 | KASQDIDRYLS | 1 | 2 |
| | L2 | RVKRLVD | 2 | |
| | L3 | VQYDEFPYT | 17 | |
| | H1 | GYTFSRYWIE | 4 | |
| | H2 | EILPGSGDINYNEKFKG | 21 | |
| | H3 | VYYDYDYGFDY | 9 | |
| U24 | L1 | KASQDIDRYLS | 1 | 10 |
| | L2 | RVKRLVD | 2 | |
| | L3 | IQYDEFPYT | 15 | |
| | H1 | GYTFSRYWIE | 4 | |
| | H2 | EILPGTGDINYNEKFKG | 18 | |
| | H3 | VYYDYDYGFDN | 14 | |
| U25 | L1 | KASQDIDRYLS | 1 | 0.5 |
| | L2 | RVKRLVD | 2 | |
| | L3 | IQYDEFNYT | 13 | |
| | H1 | GYTFSRYWIE | 4 | |
| | H2 | EILPGSGDINYNEKFKG | 21 | |
| | H3 | VYYDYDYGFDN | 14 | |
| U26 | L1 | KFSQDIDRYLT | 22 | 2 |
| | L2 | RVKRLVD | 2 | |
| | L3 | IQYDEFPYT | 15 | |
| | H1 | GYTFSRYWIE | 4 | |
| | H2 | EILPGSGNINYNEKFKG | 23 | |
| | H3 | VYYDYDYGFDY | 9 | |
| U27 | L1 | KFSQDIDRYLT | 22 | 2 |
| | L2 | RVKRLVD | 2 | |
| | L3 | IQYDEFPYT | 15 | |
| | H1 | GYTFDRYWIE | 10 | |
| | H2 | EILPGSGDINYNEKFKG | 21 | |
| | H3 | VYYDYDYGFDY | 9 | |
| U28 | L1 | KASQDIDRYLT | 12 | 2 |
| | L2 | RVKRLVD | 2 | |
| | L3 | VQYDEFPYT | 17 | |
| | H1 | GYTFDRYWIE | 10 | |
| | H2 | EILPGSGDINYNEKFKG | 21 | |
| | H3 | VYYDYDQGFDN | 24 | |
| U29 | L1 | KASQDIDRYLT | 12 | 1 |
| | L2 | RVKRLVD | 2 | |
| | L3 | VQYDEFNYT | 7 | |
| | H1 | GYTFSRYWIE | 4 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
| | H2 | EILPGSGDINYNEKFKG | 21 | |
| | H3 | VYYDYYGFDN | 14 | |
| U30 | L1 | KASQDIDRYLS | 1 | 5 |
| | L2 | RVKRLVD | 2 | |
| | L3 | VQYDEFPYT | 17 | |
| | H1 | GYTFDRYWIE | 10 | |
| | H2 | EILPGSGDINYNEKFKG | 21 | |
| | H3 | VYYDYYGFDN | 14 | |
| U31 | L1 | KFSQDIDRYLT | 22 | 1 |
| | L2 | RVKRLVD | 2 | |
| | L3 | VQYDEFPYT | 17 | |
| | H1 | GYTFSRYWIE | 9 | |
| | H2 | EILPGSGDINYNEKFKG | 21 | |
| | H3 | VYYDYYGFDN | 14 | |
| U32 | L1 | KFSQDIDRYLT | 22 | 1 |
| | L2 | RVKRLVD | 2 | |
| | L3 | IQYDEFPYT | 15 | |
| | H1 | GYTFDRYWIE | 10 | |
| | H2 | EILPGSGDINYNEKFKG | 21 | |
| | H3 | VYYDYYGFDN | 14 | |
| U33 | L1 | KFSQDIDRYLT | 22 | 1 |
| | L2 | RVKRLVD | 2 | |
| | L3 | VQYDEFPYL | 25 | |
| | H1 | GYTFDRYWIE | 10 | |
| | H2 | EILPGSGNINYNEKFKG | 23 | |
| | H3 | VYYDYYGFDN | 14 | |
| U34 | L1 | KFSQDIDRYLT | 22 | 0.2 |
| | L2 | RVKRLVD | 2 | |
| | L3 | VQYDEFPYT | 17 | |
| | H1 | GYTFDRYWIE | 10 | |
| | H2 | EILPGSGNINYNEKFKG | 23 | |
| | H3 | VYYDYYGFTY | 26 | |
| U35 | L1 | KASQDIDRYLT | 12 | 1 |
| | L2 | RVKRLVD | 2 | |
| | L3 | VQYDEFPYL | 25 | |
| | H1 | GYTFDRYWIE | 10 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
| | H2 | EILPGTGTINYNEKFKG | 8 | |
| | H3 | VYYDYYGFTN | 27 | |
| U36 | L1 | KASQDIDRYLT | 12 | 5 |
| | L2 | RVKRLVD | 2 | |
| | L3 | VQYDEFPYT | 17 | |
| | H1 | GYTFDRYWIE | 10 | |
| | H2 | EILPGSGDINYNEKFKG | 21 | |
| | H3 | VYYDYYGFTY | 26 | |
| U37 | L1 | KFSQDIDRYLT | 22 | 2 |
| | L2 | RVKRLVD | 2 | |
| | L3 | VQYDEFPYT | 17 | |
| | H1 | GYTFSRYWIE | 4 | |
| | H2 | EILPGSGDINYNEKFKG | 21 | |
| | H3 | VYYDYYGFDY | 9 | |
| U38 | L1 | KASQDIDRYLT | 12 | 1 |
| | L2 | RVKRLVD | 2 | |
| | L3 | VQYDEFNYT | 7 | |
| | H1 | GYTFSRYWIE | 4 | |
| | H2 | EILPGTGDINYNEKFKG | 18 | |
| | H3 | VYYDYYGFDN | 14 | |
| U39 | L1 | KFSQDIDRYLT | 22 | 2 |
| | L2 | RVKRLVD | 2 | |
| | L3 | IQYDEFPYT | 15 | |
| | H1 | GYTFSRYWIE | 4 | |
| | H2 | EILPGTGDINYNEKFKG | 18 | |
| | H3 | VYYDYYGFDN | 14 | |
| U40 | L1 | KFSQDIDRYLT | 22 | 1 |
| | L2 | RVKRLVD | 2 | |
| | L3 | IQYDEFPYL | 20 | |
| | H1 | GYTFSRYWIE | 4 | |
| | H2 | EILPGTGDINYNEKFKG | 18 | |
| | H3 | VYYDYYGFDL | 11 | |
| U41 | L1 | KFSQDIDRYLT | 22 | 1 |
| | L2 | RVKRLVD | 2 | |
| | L3 | VQYDEFPYT | 17 | |
| | H1 | GYTFSRYWIE | 4 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
| | H2 | EILPGTGNINYNEKFKG | 28 | |
| | H3 | VYYDYDYGFTL | 19 | |
| U43 | L1 | KASQDIDRFLS | 29 | 10 |
| | L2 | RVKRLVD | 2 | |
| | L3 | VQYDEFPYT | 17 | |
| | H1 | GYTFDRYWIE | 10 | |
| | H2 | EILPGSGDINYNEKFKG | 21 | |
| | H3 | MYYDYDQGFSL | 30 | |
| U44 | L1 | KASQDIDRFLT | 31 | 5 |
| | L2 | RVKRLVD | 2 | |
| | L3 | IQYDEFPYT | 15 | |
| | H1 | GYTFDRYWIE | 10 | |
| | H2 | EILPGSGTINYNEKFKG | 16 | |
| | H3 | MYYDYDQGFTN | 32 | |
| V3 | L1 | KASQDIDRFLS | 33 | 5 |
| | L2 | RVKRLVD | 2 | |
| | L3 | VQYDEFPYT | 17 | |
| | H1 | GYTFDRYWIE | 10 | |
| | H2 | EILPGSGDINYNEKFKG | 21 | |
| | H3 | MYYDYDQGFSL | 30 | |
| V4 | L1 | KASQDIDRFLT | 31 | 10 |
| | L2 | RVKRLVD | 2 | |
| | L3 | VQYDEFAYT | 34 | |
| | H1 | GYTFDRYWIE | 10 | |
| | H2 | EILPGSGDINYNEKFKG | 21 | |
| | H3 | MYYDYDQGFDY | 35 | |
| V5 | L1 | KASQDIDRFLT | 31 | 5 |
| | L2 | RVKRLVD | 2 | |
| | L3 | LQYDEFPYT | 3 | |
| | H1 | GYTFDRYWIE | 10 | |
| | H2 | EILPGTGTINYNEKFKG | 8 | |
| | H3 | MYYDYDQGFDN | 36 | |
| V6 | L1 | KASQDIDRYLT | 12 | 3 |
| | L2 | RVKRLVD | 2 | |
| | L3 | VQYDEFPYT | 17 | |
| | H1 | GYTFDRYWIE | 10 | |
| | H2 | EILPGTGTINYNEKFKG | 8 | |
| | H3 | VYYDYDYGFDN | 14 | |
| V7 | L1 | KASQDIDRYLT | 12 | 2 |
| | L2 | RVKRLVD | 2 | |
| | L3 | VQYDEFPYT | 17 | |
| | H1 | GYTFSRYWIE | 4 | |
| | H2 | EILPGTGDINYNEKFKG | 18 | |
| | H3 | VYYDYDYGFDN | 14 | |
| V8 | L1 | KASQDIDRYLT | 12 | 3 |
| | L2 | RVKRLVD | 2 | |
| | L3 | IQYDEFPYT | 15 | |
| | H1 | GYTFDRYWIE | 10 | |
| | H2 | EILPGTGTINYNEKFKG | 8 | |
| | H3 | VYYDYDYGFDY | 9 | |
| W1 | L1 | KASQDIDRYLT | 12 | 2 |
| | L2 | RVKRLVD | 2 | |
| | L3 | VQYDEFNYT | 7 | |
| | H1 | GYTFSRYWIE | 4 | |
| | H2 | EILPGSGDINYNEKFKG | 21 | |
| | H3 | VYYDYDYGFDN | 14 | |
| W2 | L1 | KFSQDIDRYLT | 22 | 4 |
| | L2 | RVKRLVD | 2 | |
| | L3 | VQYDEFPYT | 17 | |
| | H1 | GYTFDRYWIE | 10 | |
| | H2 | EILPGTGDINYNEKFKG | 18 | |
| | H3 | VYYDYDYGFDN | 14 | |
| W3 | L1 | KASQDIDRFLT | 31 | 10 |
| | L2 | RVKRLVD | 2 | |
| | L3 | LQYDEFPYT | 3 | |
| | H1 | GYTFDRYWIE | 10 | |
| | H2 | EILPGSGDINYNEKFKG | 21 | |
| | H3 | MYYDYDQGFDY | 35 | |
| W4 | L1 | KASQDIDRFLT | 31 | 10 |
| | L2 | RVKRLVD | 2 | |
| | L3 | LQYDEFPYT | 3 | |
| | H1 | GYTFDRYWIE | 10 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
| W5 | H2 | EILPGTGTINYNEKFKG | 8 | |
| | H3 | MYYDYDQGFDY | 35 | |
| | L1 | KFSQDIDRFLT | 37 | 10 |
| | L2 | RVKRLVD | 2 | |
| | L3 | VQYDEFPYT | 17 | |
| W6 | H1 | GYTFSRYWIE | 4 | |
| | H2 | EILPGSGDINYNEKFKG | 21 | |
| | H3 | MYYDYDQGFSL | 30 | |
| | L1 | KFSQDIDRFLT | 37 | 5 |
| | L2 | RVKRLVD | 2 | |
| | L3 | VQYDEFPYT | 17 | |
| W8 | H1 | GYTFDRYWIE | 10 | |
| | H2 | EILPGTGTINYNEKFKG | 8 | |
| | H3 | MYYDYDQGFTN | 32 | |
| | L1 | KASQDIDRFLT | 31 | 5 |
| | L2 | RVKRLVD | 2 | |
| | L3 | IQYDEFPYT | 15 | |
| W9 | H1 | GYTFSRYWIE | 4 | |
| | H2 | EILPGSGTINYNEKFKG | 16 | |
| | H3 | MYYDYDQGFDY | 35 | |
| | L1 | KASQDIDRFLT | 31 | 5 |
| | L2 | RVKRLVD | 2 | |
| | L3 | VQYDEFPYT | 17 | |
| W12 | H1 | GYTFSRYWIE | 4 | |
| | H2 | EILPGSGDINYNEKFKG | 21 | |
| | H3 | MYYDYDQGFDL | 38 | |
| | L1 | KFSQDIDRFLS | 39 | 10 |
| | L2 | RVKRLVD | 2 | |
| | L3 | VQYDEFPYT | 17 | |
| W13 | H1 | GYTFDRYWIE | 10 | |
| | H2 | EILPGSGNINYNEKFKG | 23 | |
| | H3 | MYYDYDQGFTL | 40 | |
| | L1 | KFSQDIDRFLT | 37 | 15 |
| | L2 | RVKRLVD | 2 | |
| | L3 | IQYDEFPYT | 15 | |
| W14 | H1 | GYTFDRYWIE | 10 | |
| | H2 | EILPGSGDINYNEKFKG | 21 | |
| | H3 | MYYDYDQGFDY | 35 | |
| | L1 | KFSQDIDRFLS | 39 | 10 |
| | L2 | RVKRLVD | 2 | |
| | L3 | VQYDEFPYG | 41 | |
| W17 | H1 | GYTFSRYWIE | 4 | |
| | H2 | EILPGTGDINYNEKFKG | 18 | |
| | H3 | MYYDYDQGFDN | 36 | |
| | L1 | KFSQDIDRFLS | 39 | 20 |
| | L2 | RVKRLVD | 2 | |
| | L3 | VQYDEFPYG | 41 | |
| W18 | H1 | GYTFDRYWIE | 10 | |
| | H2 | EILPGSGDINYNEKFKG | 21 | |
| | H3 | MYYDYDQGFDL | 38 | |
| | L1 | KFSQDIDRFLS | 39 | 10 |
| | L2 | RVKRLVD | 2 | |
| | L3 | VQYDEFPYT | 17 | |
| W19 | H1 | GYTFDRYWIE | 10 | |
| | H2 | EILPGSGTINYNEKFKG | 16 | |
| | H3 | MYYDYDQGFDN | 36 | |
| | L1 | KFSQDIDRFLS | 39 | 10 |
| | L2 | RVKRLVD | 2 | |
| | L3 | VQYDEFPYT | 17 | |
| W20 | H1 | GYTFSRYWIE | 4 | |
| | H2 | EILPGSGNINYNEKFKG | 23 | |
| | H3 | MYYDYDQGFTY | 42 | |
| | L1 | KFSQDIDRFLS | 39 | 10 |
| | L2 | RVKRLVD | 2 | |
| | L3 | VQYDEFPYT | 17 | |
| W21 | H1 | GYTFDRYWIE | 10 | |
| | H2 | EILPGSGDINYNEKFKG | 21 | |
| | H3 | MYYDYDQGFDY | 35 | |
| | L1 | KFSQDIDRFLT | 37 | 8 |
| | L2 | RVKRLVD | 2 | |
| | L3 | IQYDEFPYT | 15 | |
| | H1 | GYTFDRYWIE | 10 | |

TABLE 2-continued

Sequences of CDRs tending to induce high potency in antibodies

| Clone | CDR | Sequence | SEQ ID NO. | IC$_{50}$ wt/Fab |
|---|---|---|---|---|
|  | H2 | EILPGSGTINYNEKEKG | 16 |  |
|  | H3 | MYYDYDQGFDY | 35 |  |
| W22 | L1 | KASQDIDRFLT | 31 | 5 |
|  | L2 | RVKRLVD | 2 |  |
|  | L3 | VQYDEFPYT | 17 |  |
|  | H1 | GYTFDRYWIE | 10 |  |
|  | H2 | EILPGTGTINYNEKLFKG | 8 |  |
|  | H3 | MYYDYDQGFDY | 35 |  |

In specific embodiments, the present invention relates to an isolated antibody comprising a $K_d$ of at least $10^{-11}$ M and most preferably at least $10^{-12}$ M and wherein the $k_{off}$ is at least about $10^{-3}$ s$^{-1}$, preferably at least about $5 \times 10^{-4}$ s$^{-1}$, and most preferably at least $1 \times 10^{-4}$ s$^{-1}$ (including all combinations thereof).

Preferred antibodies of the present invention that bind to mature human IL-1β with a $K_d$ of $1 \times 10^{-11}$ or less, have a $k_{off}$ rate constant of $1 \times 10^{-3}$ s$^{-1}$ or less, neutralize human IL-1β activity, and in which deamidation is eliminated at position 55 of HCDR2, are selected from the group consisting of SEQ ID NOS: 45-54.

Standard approaches to characterizing and synthesizing the CDR libraries of single mutations were used (see Wu et al, Proc. Natl. Acad. Sci. U.S.A 95: 6037-6042 (1998)). The target CDR was first deleted for each of the libraries prior to annealing the nucleotides. For synthesis of the libraries, the CDRs of a reference antibody (see FIGS. 1&2) were defined as in Table 1. Codon based mutagenesis for oligonucleotide synthesis to yield the CDR sequences of the invention was employed.

Libraries were initially screened by capture lift to identify the highest affinity variants. The capture lift procedure (Watkins, Methods Mol. Biol. 178:187-193, (2002)) is known in the art and is as described in WO/0164751 and US2002/0098189. Subsequently, these clones were further characterized using capture ELISA and by titration on immobilized antigen. Following such screening, the antibodies are then screened for their respective $k_{off}$ values, the positive effects of which are then measured by determination of potency.

The antibodies disclosed herein contain CDRs differing from those of Mu007 in complementarity determining regions L1 (or LCDR1), L3 (or LCDR3), H1 (or HCDR1), H2 (HCDR2) and H3 (or HCDR3).

CDRs of selected Fab fragments are shown in Table 2 (all of which have the framework sequences of FIGS. 3&4) where the reference clone is the clone with heavy and light chain variable region sequences shown in FIGS. 1&2 (SEQ ID NOS: 43 and 44 for the light and heavy chain sequences, respectively).

In accordance with the invention, by combining such amino acid substitutions so that more than one occurred in the same antibody molecule, it was possible to greatly increase the potency of the antibodies disclosed herein.

In general, there is a correlation between low $k_{off}$ and potency of the antibody, with all of the lower $k_{off}$ variants having more than one beneficial CDR, including having up to five CDRs substituted.

The combinations of CDR sequences disclosed in Table 2 can be present in whole tetrameric antibody molecules or in active fragments, such as Fab fragment. The potency data for clones shown in Table 2 are for Fab fragments while the data for clones shown in Table 4 are for whole antibody molecules compared to the reference antibody, Mu007.

The antibodies of the invention can be present in a relatively pure or isolated form as well as in a supernatant drawn from cells grown in wells or on plates. The antibodies of the invention can thus also be present in the form of a composition comprising the antibody of the invention and wherein said antibody is suspended in a pharmacologically acceptable diluent or excipient. The antibodies of the invention may be present in such a composition at a concentration, or in an amount, sufficient to be of therapeutic or pharmacological value in treating or preventing diseases (for example, preventing rheumatoid arthritis and osteoarthritis). The antibodies may also be present in a composition in a more dilute form.

DNA encoding the antibodies of the present invention will typically further include an expression control polynucleotide sequence operably linked to the antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the light chains, heavy chains, light/heavy chain dimers or intact antibodies, binding fragments or other immunoglobulin forms.

The nucleic acid sequences of the present invention capable of ultimately expressing the desired antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

As described herein, in addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce $F(ab')_2$ fragments. Single chain antibodies may be produced by joining VL and VH with a DNA linker.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, plant cells may also be used for expression. Optimal methods of plant transformation vary depending on the type of plant. For example, see WO00/53794.

Mammalian tissue cell culture may also be used to express and produce the polypeptides of the present invention. Eukaryotic cells are actually preferred, because a number of suitable host cell lines capable of secreting intact immunoglobulins have been developed in the art, and include the CHO cell lines, various COS cell lines, Syrian Hamster Ovary cell lines, HeLa cells, myeloma cell lines, transformed B-cells, human embryonic kidney cell lines, or hybridomas. Preferred cell lines are CHO and myeloma cell lines such as SP2/0 and NS0.

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. Preferred polyadenylation sites include sequences derived from SV40 and bovine growth hormone.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the antibodies can be purified according to standard procedures, including ammonium sulfate precipitation, ion exchange, affinity (e.g. Protein A), reverse phase, hydrophobic interaction column chromatography, gel electrophoresis, and the like. Substantially pure immunoglobulins having at least about 90 to 95% purity are preferred, and 98 to 99% or more purity most preferred, for pharmaceutical uses. Once purified, partially or to homogeneity as desired, the polypeptides may then be used therapeutically or prophylactically, as directed herein.

This invention also relates to a method of treating humans experiencing an IL-1β mediated inflammatory disorder which comprises administering an effective dose of an IL-1β antibody to a patient in need thereof. The antibodies of the present invention bind to and prevent IL-1β from binding an IL-1β receptor and initiating a signal. Various IL-1β-mediated disorders include rheumatoid arthritis (RA), osteoarthritis (OA), allergy, septic or endotoxic shock, septicemia, asthma, graft versus host disease, Crohn's disease, and other inflammatory bowel diseases. In addition, IL-1β mediates host defense responses to local and systemic diseases and injury and to neuroinflammation and cell death in neurodegenerative conditions, such as stroke and ischemic, excitotoxic, and traumatic head injury. IL-1β has also been implicated in chronic degenerative diseases, in particular, multiple sclerosis, Parkinson's and Alzheimer's diseases. Preferably, the IL-1β antibodies encompassed by the present invention are used to treat RA and/or OA.

Patients with RA suffer from chronic swelling and inflammation of the joints and ongoing destruction of cartilage and bone. IL-1β and TNF-α are the most critical cytokines in the pathogenesis of RA. However, while both IL-1β and TNF-α mediate inflammation, IL-1β is the primary mediator of bone and cartilage destruction. Activated monocytes and fibroblasts in the synovial tissue produce IL-1β which in turn stimulates the production of additional pro-inflammatory cytokines, prostaglandins, and matrix metalloproteases. The synovial lining becomes hypertrophied, invading and eroding bone and cartilage.

Disease-modifying antirheumatic drugs (DMARDS) such as hydroxychloroquine, oral or injectable gold, methotrexate, azathioprine, penicillamine, and sulfasalazine have been used with modest success in the treatment of RA. Their activity in modifying the course of RA is believed to be due to suppression or modification of inflammatory mediators such as IL-1β. Methotrexate, for example, at doses of 7.5 to 10 mg per week caused a reduction in IL-1β plasma concentrations in RA patients. Similar results have been seen with corticosteroids. Thus, the IL-1β antibodies of the present invention may be used alone or in combinations with DMARDS which may act to reduce IL-1β protein levels in plasma.

An effective amount of the IL-1β antibodies of the present invention is that amount which provides clinical efficacy without intolerable side effects or toxicity. Clinical efficacy for RA patients can be assessed using the American College of Rheumatology Definition of Improvement (ACR20). A patient is considered a responder if the patient shows a 20% improvement in the tender joint count, swollen joint count, and 3 of 5 other components which include patient pain assessment, patient global assessment, physician global assessment, Health Assessment Questionnaire, and serum C-reactive protein. Prevention of structural damage can be assessed by the van der Heijde modification of the Sharp Scoring system for radiographs (erosion count, joint space narrowing).

The IL-1β antibodies of the present invention can also be used to treat patients suffering from osteoarthritis (OA). OA is the most common disease of human joints and is characterized by articular cartilage loss and osteophyte formation. Clinical features include joint pain, stiffness, enlargement, instability, limitation of motion, and functional impairment. OA has been classified as idiopathic (primary) and secondary forms. Criteria for classification of OA of the knee and hip have been developed by the American College of Rheumatology on the basis of clinical, radiographic, and laboratory parameters.

An effective amount of the IL-1β antibodies of the present invention is the amount which shows clinical efficacy in OA patients as measured by the improvement in pain and function as well as the prevention of structural damage. Improvements in pain and function can be assessed using the pain and physical function subscales of the WOMAC OA Index. The index probes clinically important patient-relevant symptoms in the areas of pain, stiffness, and physical function. Prevention of structural damage can be assessed by measuring joint space width on radiographs of the knee or hip.

Since elevated levels of IL-1β have been implicated in human neuro-degenerative conditions such as stroke and brain injury (Rothwell, N. J., et al., *TINS* 23(12): 618-625, 2000), the anti-IL-1β antibodies encompassed by the present invention can also be used to treat neuroinflammation associated with stroke and ischemic, excitotoxic, and traumatic head injury.

The antibodies of the present invention are administered using standard administration techniques, preferably peripherally (i.e., not by administration into the central nervous system) by intravenous, intraperitoneal, subcutaneous, pulmonary, transdermal, intramuscular, intranasal, buccal, sublingual, or suppository administration.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents and the like are used as appropriate. *Remington's Pharmaceutical Sciences*, Mack Publishing Co., Easton Pa., latest edition, incorporated herein by reference, provides a compendium of formulation techniques as are generally known to practitioners.

The concentration of the IL-1β antibody in formulations may be from as low as about 0.1% to as much as 15 or 20% by weight and will be selected primarily based on fluid volumes, viscosities, stability, and so forth, in accordance with the particular mode of administration selected. Preferred concentrations of the IL-1β antibody will generally be in the range of 1 to about 100 mg/mL. Preferably, 10 to about 50 mg/mL.

The formulation may include a buffer. Preferably the buffer is a citrate buffer or a phosphate buffer or a combination thereof. Generally, the pH of the formulation is between about 4 and about 8. Preferably, the pH is between about 5 and about 7.5. The pH of the formulation can be selected to balance antibody stability (chemical and physical) and comfort to the patient when administered. The formulation may also include a salt such as NaCl. In addition, the formulation may include a detergent to prevent aggregation and aid in maintaining stability.

The formulation may be sterile filtered after making the formulation, or otherwise made microbiologically acceptable. A preservative such as m-cresol or phenol, or a mixture thereof may be added to prevent microbial growth and contamination.

A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g., with conventional immunoglobulins, IgM antibodies tend to have greater activity loss than IgG antibodies). Dosages may have to be adjusted to compensate.

Although the foregoing methods appear to be the most convenient and most appropriate for administration of proteins such as humanized antibodies, by suitable adaptation, other techniques for administration, such as transdermal administration and oral administration may be employed provided proper formulation is designed. In addition, it may be desirable to employ controlled release formulations using biodegradable films and matrices, or osmotic mini-pumps, or delivery systems based on dextran beads, alginate, or collagen. In summary, formulations are available for administering the antibodies of the invention and may be chosen from a variety of options.

Typical dosage levels can be optimized using standard clinical techniques and will be dependent on the mode of administration and the condition of the patient. Generally, doses will be in the range of 10 µg/kg/month to 10 mg/kg/month.

The invention is illustrated by the following examples that are not intended to be limiting in any way.

EXAMPLE 1

Binding Affinity and Specificity

Affinities and specificities of Mu007 and antibodies of the present invention were determined using BIAcore measurements (Table 3). BIAcore™ is an automated biosensor system that measures molecular interactions. (Karlsson, et al. (1991) *J. Immunol. Methods* 145: 229-240). In these experiments antibody was captured to a surface at low density on a BIAcore™ chip. Ethyl-dimethylaminopropyl-carbodiimide (EDC) was used to couple reactive amino groups to protein A to a flow cell of a carboxy-methyl (CM5) BIAcore™ sensor chip. Protein A was diluted in sodium acetate buffer, pH 4.5, and immobilized on a flow cell of a CM5 chip using EDC to yield 1000 response units. Unreacted sites were blocked with ehanolamine. A flow rate of 60 µl/min was used. Multiple binding/elution cycles were performed by injection a 10 µl solution of 2 µg/mL of the antibodies of the present invention followed by human IL-1β at decreasing concentrations for each cycle (e.g. 1500, 750, 375, 188, 94, 47, 23.5, 12, and 0 picomolar). Elution was performed with glycine-HCl, pH 1.5. BIAevaluation™ was used to analyze the kinetic data. The protocol utilized for determining the affinity of Mu007 is as described in PCT/US02/21281.

TABLE 3

Binding properties of anti-IL-1β antibodies to human IL-1β determined by BIAcore (HBS-EP buffer, pH 7.4 at 25° C.)

| CLONE | $k_{on}$ (M$^{-1}$ s$^{-1}$) | $k_{off}$ (s$^{-1}$) | $K_d$ (M) |
|---|---|---|---|
| W17 (IgG1) | 3.1e7 | 0.9e−4 | 2.8e−12 |
| U43 (IgG1) | 4.7e7 | 2.2e−4 | 4.7e−12 |
| W13 (IgG1) | 6.1e7 | 1.7e−4 | 2.8e−12 |
| W18 (IgG1) | 4.1e7 | 1.8e−4 | 4.2e−12 |
| W20 (IgG1) | 3.8e7 | 1.0e−4 | 2.7e−12 |
| Mu007 | 2.6e7 | 1.6e−4 | 6.2e−12 |
| W17 (IgG4) | 3.2e7 | 1.0e−4 | 3.3e−12 |

EXAMPLE 2

Antibody Potency

A murine cell requiring low levels of IL-1β for proliferation was used to determine the ability of the antibodies of the present invention and Mu007 to neutralize human IL-1β. T1165.17 cells that were no longer in log phase growth were washed 3 times with RPMI 1640 (GibcoBRL Cat. #22400-089) supplemented with 10% fetal calf serum (GibcoBRL Cat. #10082-147), 1 mM sodium pyruvate, 50 μM beta mercaptoethanol, and an antibiotic/antimycotic (GibcoBRL Cat. #15240-062). Cells were plated at 5,000 cells per well of a 96 well plate. Human IL-1β was present at a constant level of 0.3 μM and a dilution series of antibody was added. Cells were incubated for 20 hours in a 37° C./5% $CO_2$ incubator at which point 1 μCi $^3$H-thymidine was added per well and plates incubated an additional 4 hours in the incubator. Cells were harvested and incorporated radioactivity determined by a scintillation counter. Table 4 illustrates inhibition of IL-1β stimulated proliferation by Mu007 and the antibodies of the present invention (IgG isotypes as indicated).

TABLE 4

$IC_{50}$ Measured in the T1165.17 Cell Proliferation Assay

| SAMPLE | $IC_{50}$ pM | Fold Increase in Potency |
|---|---|---|
| Mu007 | 20.6 ± 0.5 | 1 |
| W17 (IgG1) | 1.8 ± 0.3 | 11 |
| U43 (IgG1) | 4.0 ± 0.2 | 5 |
| W18 (IgG1) | 2.0 ± 0.1 | 10 |
| W13 (IgG1) | 1.2 ± 0.1 | 17 |
| W20 (IgG1) | 1.2 ± 0.1 | 17 |
| W17 (IgG4) | 1.7 ± 0.1 | 12 |

EXAMPLE 3

Neutralization of Human IL-1β in vivo

Human IL-1β is able to bind and stimulate the mouse IL-1β receptor, leading to an elevation of mouse IL-6. Time and dose ranging experiments were undertaken to identify the optimal dose of human IL-1β and the optimal time for induction of mouse IL-6. These experiments indicated that a 3 μg/kg dose of human IL-1β and a time of 2 hours post IL-1β administration gave maximal levels of IL-6 in mouse serum. The antibodies of the present invention were administered IV to mice at 13, 27, 81, and 270 μg/kg, one hour prior to an s.c. injection of human IL-1β. At two hours post IL-1β administration, mice were sacrificed, and IL-6 levels were determined by ELISA. Isotype matched antibodies were used as negative controls. The antibodies of the present invention blocked the effects of IL-1β to stimulate the mouse IL-1β receptor, leading to an elevation of mouse IL-6, in a dose dependent manner (Table 5).

TABLE 5

| Antibody | IL-6 Serum Levels pg/ml | Std Dev. |
|---|---|---|
| IL-1β Ctl. (3 μg/kg) | 462.0 | 279.1 |
| Human IgG Ctl (270 μg/kg) | 1.0 | 1.0 |
| IL-1β Ctl. (3 μg/kg) + Human IgG Ctl (270 μg/kg) | 592.3 | 303.0 |
| W13 Ctl. (270 μg/kg) | 4.1 | 2.4 |

TABLE 5-continued

| Antibody | IL-6 Serum Levels pg/ml | Std Dev. |
|---|---|---|
| W17 Ctl. (270 μg/kg) | 3.2 | 2.9 |
| W18 Ctl. (270 μg/kg) | 5.2 | 2.4 |
| U43 Ctl. (270 μg/kg) | 1.3 | 1.0 |
| IL-1β (3 μg/kg) + W13 Ctl. (13 μg/kg) | 655.4 | 78.0 |
| IL-1β (3 μg/kg) + W13 Ctl. (27 μg/kg) | 277.4 | 97.3 |
| IL-1β (3 μg/kg) + W13 Ctl. (81 μg/kg) | 129.2 | 20.2 |
| IL-1β (3 μg/kg) + W13 Ctl. (270 μg/kg) | 23.4 | 5.3 |
| IL-1β (3 μg/kg) + W17 Ctl. (13 μg/kg) | 566.8 | 294.0 |
| IL-1β (3 μg/kg) + W17 Ctl. (27 μg/kg) | 410.1 | 107.5 |
| IL-1β (3 μg/kg) + W17 Ctl. (81 μg/kg) | 113.7 | 42.3 |
| IL-1β (3 μg/kg) + W17 Ctl. (270 μg/kg) | 27.5 | 19.6 |
| IL-1β (3 μg/kg) + W18 Ctl. (13 μg/kg) | 398.5 | 143.2 |
| IL-1β (3 μg/kg) + W18 Ctl. (27 μg/kg) | 231.8 | 32.2 |
| IL-1β (3 μg/kg) + W18 Ctl. (81 μg/kg) | 77.9 | 24.7 |
| IL-1β (3 μg/kg) + W18 Ctl. (270 μg/kg) | 18.0 | 5.9 |
| IL-1β (3 μg/kg) + U43 Ctl. (13 μg/kg) | 755.7 | 299.7 |
| IL-1β (3 μg/kg) + U43 Ctl. (27 μg/kg) | 509.3 | 99.6 |
| IL-1β (3 μg/kg) + U43 Ctl. (81 μg/kg) | 186.4 | 80.8 |
| IL-1β (3 μg/kg) + U43 Ctl. (270 μg/kg) | 39.3 | 17.7 |

EXAMPLE 4

Antibody Expression

The following protocol applies to the expression of any of the antibodies of the present invention.

Expression vectors encoding a leader sequence, and either the constant region for Kappa light chain or Gamma 1 heavy chain were used to clone Fab sequences, resulting in full antibody genes. The vectors can be used in multiple mammalian cell lines for both transient and stable expression.

The vectors are scaled up to generate the amount of DNA needed to support the transfection. The final DNA remains as a closed circular vector when used in transient transfections, and can be linerized when used in a stable transfection. Small-scale transient transfections should be supported to identify the best ratio of LC:HC. In either transfection the vector encoding the light chain (LC) and the heavy chain (HC) are mixed together prior to being transfected into the cells.

The transient transfection is supported in HEK 293 EBNA cells. The transfection is scaled up and cultured for five to seven days post transfection. The supernatant is harvested, and the antibody is purified using conventional approaches for antibodies.

Stable transfections into CHO (Chinese Hamster Ovary)-DG44 cells can be supported using the vectors outlined. The amount of DNA used can vary from 20 μg to 200 μg. The cells ($10^7$) are transfected using a BioRad Gene Pulsar II set at 360 V/950 uF. The cells are recovered for 24-72 hours at 37° C./5% CO2, and then plated under selection (medium w/o hypoxanthine and thymidine, and with varying levels of methotrexate, MTX, for additional pressure).

Stable transfections into NS0 (mouse myeloma) cells can be supported by moving the genes for the LC and HC into expression vectors encoding a glutamine syiithetase gene. The amount of DNA used is 40 ug total. The cells ($10^7$) are transfected using a BioRad Gene Pulsar II machine set at 300V/1000 uF. The cells are recovered for 24-72 hours at 37° C./10% CO2 and then plated under selection (medium w/o glutamine and with methionine sulphoximine, MSX, for additional pressure).

Plating for both types of cell lines is supported in 96-well plates at seed densities specific for the cell line (500c/w CHO-DG44, 2000c/w NS0). When visible colony formation is noted in the wells, the plates can be screened for antibody production using ELISA based methods. The wells containing cells with a positive signal for antibody are expanded into 24-well plates. The lines are cultured and evaluated under expression experiments to identify a candidate cell line with acceptable titer and protein quality. The goal of the cell line generation effort is to identify a clone that can be scaled in serum free culture conditions with acceptable titer, growth characteristic and product quality profile.

We claim

1. An isolated nucleic acid comprising a polynucleotide encoding an antibody, or an antigen-binding portion thereof, that specifically binds human IL-1β, comprising a polynucleotide encoding a light chain variable region and a polynucleotide encoding a heavy chain variable region selected from the group consisting of:
   (a) a light chain variable region of SEQ ID NO:60, and a heavy chain variable region of SEQ ID NO:55;
   (b) a light chain variable region of SEQ ID NO:61, and a heavy chain variable region of SEQ ID NO:56;
   (c) a light chain variable region of SEQ ID NO:62, and a heavy chain variable region of SEQ ID NO:57;
   (d) a light chain variable region of SEQ ID NO:63, and a heavy chain variable region of SEQ ID NO:59; and,
   (e) a light chain variable region of SEQ ID NO:64, and a heavy chain variable region of SEQ ID NO:58.

2. An expression vector comprising the nucleic acid according to claim 1.

3. A host cell stably transfected with the expression vector of claim 2.

4. A process for producing an antibody or antigen binding portion thereof, comprising culturing the host cell of claim 3, and recovering the antibody or antigen binding portion thereof encoded by said polynucleotide from the culture.

5. An isolated nucleic acid, comprising a polynucleotide encoding an antibody or antigen binding portion thereof, that specifically binds human IL-1β, wherein said polynucleotide encodes the amino acid sequences of the light and heavy chains selected from the group consisting of:
   (a) a light chain of SEQ ID NO:46 and a heavy chain of SEQ ID NO: 45;
   (b) a light chain SEQ ID NO:48 and a heavy chain of SEQ ID NO: 47;
   (c) a light chain of SEQ ID NO:48 and a heavy chain of SEQ ID NO:68;
   (d) a light chain of SEQ ID NO:50 and a heavy chain of SEQ ID NO:49;
   (e) a light chain of SEQ ID NO:52 and a heavy chain of SEQ ID NO: 51; and,
   (f) a light chain of SEQ ID NO:54 and a heavy chain of SEQ ID NO:53.

6. An expression vector comprising the nucleic acid according to claim 5.

7. A host cell stably transfected with the expression vector of claim 6.

8. A process for producing an antibody or antigen binding portion thereof, comprising culturing the host cell of claim 7 and recovering the antibody or antigen binding portion thereof encoded by said polynucleotide from the culture.

* * * * *

UNITED STATES PATENT AND TRADEMARK OFFICE
CERTIFICATE OF CORRECTION

| | | |
|---|---|---|
| PATENT NO. | : 7,714,120 B2 | Page 1 of 1 |
| APPLICATION NO. | : 12/428558 | |
| DATED | : May 11, 2010 | |
| INVENTOR(S) | : Craig Duane Dickinson et al. | |

It is certified that error appears in the above-identified patent and that said Letters Patent is hereby corrected as shown below:

The priority is not correctly reflected on the face of the patent.
Insert on Front Page of patent:

Related U.S. Application Data
Delete "Division of application No. 10/542,508, filed as application No. PCT/US2004/000019 on Jan. 24, 2004, now Pat. No.7,541,033", and insert --This application is a divisional of U.S. Ser. No. 10/542,508, filed Jul. 15, 2005, which is a 371 of PCT/US2004/000019, filed Jan. 21, 2004, now U.S. Pat. No. 7,541,033, which claims priority of U.S. Provisional application No. 60/442,798 filed on Jan. 24, 2003.--

In First Page, Column 1 (Assignee), line 1, delete "Molecule" and insert --Molecular--

In Column 1, line 4, delete "2005" and insert --2005,--

In Column 1, line 5, insert after Pat. No. 7,541,033 --, which claims priority of U.S. Provisional application No. 60/442,798 filed on Jan. 24, 2003.--

In Column 81, Claim 1, line 30, delete "NO:60," and insert --NO:60--

In Column 81, Claim 1, line 32, delete "NO:61," and insert --NO:61--

In Column 81, Claim 1, line 35, delete "NO:62," and insert --NO:62--

In Column 81, Claim 1, line 37, delete "NO:63," and insert --NO:63--

In Column 81, Claim 1, line 39, delete "NO:64," and insert --NO:64--

In Column 81, Claim 4, line 46, delete "claim 3," and insert --claim 3--

Signed and Sealed this

Twentieth Day of July, 2010

David J. Kappos
*Director of the United States Patent and Trademark Office*